United States Patent
Driscoll

(10) Patent No.: US 9,642,826 B2
(45) Date of Patent: *May 9, 2017

(54) OMEGA-3 ENRICHED FISH OIL-IN-WATER PARENTERAL NUTRITION EMULSIONS

(71) Applicant: STABLE SOLUTIONS LLC, Goleta, CA (US)

(72) Inventor: David F. Driscoll, Bridgewater, MA (US)

(73) Assignee: STABLE SOLUTIONS LLC, Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/715,075

(22) Filed: May 18, 2015

(65) Prior Publication Data

US 2015/0246013 A1 Sep. 3, 2015

Related U.S. Application Data

(63) Continuation of application No. 13/255,828, filed as application No. PCT/US2010/000723 on Mar. 11, 2010, now Pat. No. 9,034,389, application No. 14/715,075, which is a continuation-in-part of application No. 12/382,196, filed on Mar. 11, 2009, now Pat. No. 8,241,672.

(51) Int. Cl.

| | | |
|---|---|---|
| *A61K 35/60* | (2006.01) | |
| *A23D 9/013* | (2006.01) | |
| *A23D 7/00* | (2006.01) | |
| *A61K 31/202* | (2006.01) | |
| *A23D 7/005* | (2006.01) | |
| *A23D 7/01* | (2006.01) | |
| *A61K 9/00* | (2006.01) | |
| *A61K 9/107* | (2006.01) | |
| *A61K 36/286* | (2006.01) | |
| *A61K 36/47* | (2006.01) | |
| *A61K 47/14* | (2017.01) | |
| *A61K 47/22* | (2006.01) | |
| *A61K 47/24* | (2006.01) | |
| *A23P 20/12* | (2016.01) | |
| *A23L 29/10* | (2016.01) | |
| *A23L 33/00* | (2016.01) | |
| *A23L 33/115* | (2016.01) | |
| *A23L 33/12* | (2016.01) | |
| *A23L 33/17* | (2016.01) | |

(52) U.S. Cl.
CPC .......... *A61K 31/202* (2013.01); *A23D 7/003* (2013.01); *A23D 7/0053* (2013.01); *A23D 7/011* (2013.01); *A23L 29/10* (2016.08); *A23L 33/115* (2016.08); *A23L 33/12* (2016.08); *A23L 33/17* (2016.08); *A23L 33/40* (2016.08); *A23P 20/12* (2016.08); *A61K 9/0019* (2013.01); *A61K 9/107* (2013.01); *A61K 9/1075* (2013.01); *A61K 35/60* (2013.01); *A61K 36/286* (2013.01); *A61K 36/47* (2013.01); *A61K 47/14* (2013.01); *A61K 47/22* (2013.01); *A61K 47/24* (2013.01); *A23V 2002/00* (2013.01); *A23V 2200/02* (2013.01); *A23V 2200/314* (2013.01); *A23V 2200/324* (2013.01); *A23V 2200/326* (2013.01); *A23V 2250/187* (2013.01); *A23V 2250/1868* (2013.01); *A23V 2250/1878* (2013.01)

(58) Field of Classification Search
None
See application file for complete search history.

(56) References Cited

U.S. PATENT DOCUMENTS

| | | | |
|---|---|---|---|
| 4,707,470 A * | 11/1987 | Kirsh | ............... A61K 9/1075 514/31 |
| 5,118,493 A | 6/1992 | Kelley et al. | |
| 5,278,149 A | 1/1994 | Provost et al. | |
| 5,574,065 A | 11/1996 | Trimbo | |
| 5,650,172 A | 7/1997 | Matsuda et al. | |

(Continued)

FOREIGN PATENT DOCUMENTS

| | | |
|---|---|---|
| DE | 196 48 566 A1 | 6/1997 |
| EP | 0 298 293 A2 | 1/1989 |

(Continued)

OTHER PUBLICATIONS

International Search Report (PCT/ISA/210) issued on Jan. 6, 2011, by United States Patent Office as the International Searching Authority for International Application No. PCT/US2010/000723.
Extended Search Report issued by the European Patent Office issued in corresponding European Patent Application No. 10751124.8 dated Feb. 1, 2012.
Bougnoux et al., "*Improving Outcome of Chemotherapy of Metastatic Breast Cancer by Docosahexaenoic Acid: a Phase II Trial,*" British Journal of Cancer, 2009, vol. 101, No. 12, pp. 1978-1985, Cancer Research UK.

(Continued)

*Primary Examiner* — Chris R Tate
*Assistant Examiner* — Douglas F White
(74) *Attorney, Agent, or Firm* — Buchanan Ingersoll & Rooney PC

(57) ABSTRACT

An emulsion is provided including: an oil component and a water component, the oil component including: fish oil triglycerides in an amount of about 60% to about 90% based on the weight of the oil component; wherein the fish oil triglycerides include omega-3 fatty acids, expressed as triglycerides, in an amount of at least 60%, based on the total weight of the fatty acids of the fish oil triglycerides; wherein the fish oil triglycerides include a total amount of EPA and DHA, expressed as triglycerides, of at least 45%, based on the total weight of the fatty acids of the fish oil triglycerides; and, at least one medium-chain triglyceride, wherein a total amount of the at least one medium-chain triglyceride is from about 10% to about 40% based on the weight of the oil component.

19 Claims, No Drawings

(56) References Cited

U.S. PATENT DOCUMENTS

| | | |
|---|---|---|
| 5,698,594 A | 12/1997 | Breivik et al. |
| 5,700,837 A | 12/1997 | Trimbo |
| 5,739,152 A | 4/1998 | Andersson et al. |
| 5,780,451 A | 7/1998 | DeMichele et al. |
| 5,853,740 A * | 12/1998 | Lu .................. A61K 9/113 424/400 |
| 5,874,470 A | 2/1999 | Nehne et al. |
| 5,886,037 A | 3/1999 | Klor et al. |
| 5,908,853 A * | 6/1999 | Nahoum ............. A61K 31/00 514/341 |
| 6,008,248 A | 12/1999 | Pscherer et al. |
| 6,020,020 A | 2/2000 | Cain et al. |
| 6,159,523 A | 12/2000 | Cain et al. |
| 6,284,268 B1 | 9/2001 | Mishra et al. |
| 6,319,243 B1 | 11/2001 | Becker et al. |
| 6,417,233 B1 | 7/2002 | Sears et al. |
| 6,432,439 B1 | 8/2002 | Suzuki et al. |
| 6,569,853 B1 | 5/2003 | Borisy et al. |
| 6,720,001 B2 | 4/2004 | Chen |
| 7,150,996 B2 | 12/2006 | Nicoli et al. |
| 7,199,151 B2 | 4/2007 | Shashoua |
| 7,323,206 B1 | 1/2008 | Driscoll et al. |
| 7,560,486 B2 | 7/2009 | Carpentier et al. |
| 8,241,672 B2 | 8/2012 | Driscoll |
| 8,703,725 B2 | 4/2014 | Troup et al. |
| 8,993,625 B2 | 3/2015 | Driscoll |
| 2002/0107265 A1 | 8/2002 | Chen et al. |
| 2003/0068385 A1 | 4/2003 | Moyer et al. |
| 2003/0144356 A1 | 7/2003 | Goodale |
| 2004/0053993 A1 | 3/2004 | Constantinides et al. |
| 2004/0077724 A1 | 4/2004 | Remmereit et al. |
| 2004/0087490 A1 | 5/2004 | Troup et al. |
| 2004/0142040 A1 | 7/2004 | Dong et al. |
| 2004/0247693 A1 | 12/2004 | Carpentier et al. |
| 2005/0027004 A1 | 2/2005 | Kyle et al. |
| 2005/0282840 A1 | 12/2005 | Ross et al. |
| 2006/0067952 A1 | 3/2006 | Chen |
| 2006/0127491 A1 | 6/2006 | Puder et al. |
| 2006/0211762 A1 | 9/2006 | Rongen et al. |
| 2007/0071777 A1 | 3/2007 | Bromer et al. |
| 2007/0148259 A1 | 6/2007 | Gupta |
| 2010/0233280 A1 | 9/2010 | Driscoll |
| 2011/0071090 A1 | 3/2011 | Driscoll |
| 2012/0040934 A1 | 2/2012 | Driscoll |
| 2013/0090297 A1 | 4/2013 | Troup et al. |

FOREIGN PATENT DOCUMENTS

| | | |
|---|---|---|
| EP | 0 311 091 A1 | 4/1989 |
| EP | 0 687 418 A2 | 12/1995 |
| EP | 0 780 124 A1 | 6/1997 |
| EP | 1 279 400 A1 | 1/2003 |
| EP | 1 408 931 B1 | 3/2009 |
| EP | 0863754 B2 | 12/2009 |
| JP | S61-502816 | 12/1986 |
| JP | 2-502010 | 7/1990 |
| JP | 07-227227 | 8/1995 |
| JP | 8-500332 | 1/1996 |
| JP | 2000-500769 | 1/2000 |
| JP | 2003-535057 | 1/2005 |
| JP | 2005-501828 | 1/2005 |
| JP | 2007-501253 | 1/2007 |
| JP | 2007-526943 | 9/2007 |
| WO | WO 86/00523 A1 | 1/1986 |
| WO | WO 89/02275 A1 | 3/1989 |
| WO | WO 90/08544 A1 | 8/1990 |
| WO | WO 97/19683 A1 | 6/1998 |
| WO | WO 01/49284 A1 | 7/2001 |
| WO | WO 01/89474 A2 | 11/2001 |
| WO | WO 03/009828 A1 | 2/2003 |
| WO | WO 2004/026294 A1 | 4/2004 |
| WO | WO 2005/016308 A1 | 2/2005 |
| WO | WO 2005/046669 A1 | 5/2005 |
| WO | WO 2005/084129 A2 | 9/2005 |
| WO | WO 2008/036353 A2 | 3/2008 |
| WO | WO 2010/104575 A1 | 9/2010 |

OTHER PUBLICATIONS

Driscoll, "*Lipid Injectable Emulsions: Pharmacopeial and Safety Issues*," Pharmaceutical Research, Sep. 2006, vol. 23, No. 9, pp. 1959-1969, Springer Science + Business Media, Inc.

Driscoll, Letter to the Editor, Journal of Parenteral and Enteral Nutrition, Jul./Aug. 2009, vol. 33, No. 4, pp. 451-452, Sage, The American Society for Parenteral & Enteral Nutrition.

Lowell et al., "*Postoperative Fluid Overload: Not a Benign Problem*," Crit Care Med, Jul. 1990;18(7):728-733, PubMed (Abstract only).

Mathru et al., "*Effect of Fast vs Slow Intralipid Infusion on Gas Exchange, Pulmonary Hemodynamics, and Prostaglandin Metabolism*," Clinical Investigations in Critical Care, Chest, Feb. 1991, 99, pp. 426-429, American College of Chest Physicians.

Prasertsom, et al., "*Pulmonary Vascular Resistance During Lipid Infusion in Neonates*," Arch Dis Child, 1996;74:F95-98, Children's Health Centre and Perinatal Research Centre, University of Alberta.

Ling et al., "*Inflammatory Mediators in Patients Receiving Long-Term Home Parenteral Nutrition*," Digestive Disease Science, Nov. 2001;46(11):2484-9, PubMed (Abstract only).

Driscoll et al., "*The Influence of Medium-chain Triglycerides on the Stability of All-In-One Formulations*," International Journal of Pharmaceutics, 240 (2002), pp. 1-10, Elsevier Science B.V.

Bistrian, "*Clinical Aspects of Essential Fatty Acid Metabolism; Jonathan Rhoads Lecture*," Journal of Parenteral and Enteral Nutrition, 2003, vol. 27, No. 3, pp. 168-175, Sage, The American Society for Parenteral & Enteral Nutrition.

Gura et al., "*Use of a Fish Oil-Based Lipid Emulsion to Treat Essential Fatty Acid Deficiency in a Soy Allergic Patient Receiving Parenteral Nutrition*," Clinical Nutrition, Oct. 2005;24(5):839-47, PubMed (Abstract only).

Wales et al., "*Neonatal Short Bowel Syndrome: A Cohort Study*," Journal of Pediatric Surgery, May 2005;40(5):755-62, PubMed (Abstract only).

Paquot et al., "*Fatty Liver in the Intensive Care Unit*," Curr Opin Clin Nutr Metab Care, Mar. 2005;8(2):183-87, PubMed (Abstract only).

Lee et al., "*Saturated, but Not n-6 Polyunsaturated, Fatty Acids Induce Insulin Resistance: Role of Intramuscular Accumulation of Lipid Metabolites*," J Appl Physiol, May 2006;100(5):1467-74, PubMed (Abstract only).

Gura et al., "*Reversal of Parenteral Nutrition-Associated Liver Disease in Two Infants With Short Bowel Syndrome Using Parenteral Fish Oil: Implications for Future Management*," Pediatrics, Jul. 2006, vol. 118, No. 1, pp. e197-e201, American Academy of Pediatrics.

Stanley et al., "*UK Food Standards Agency Workshop Report: The Effects of the Dietary N-6: n-3 fatty Acid Ratio on Cardiovascular Health*," British Journal of Nutrition, Dec. 2007; 98(6):1305-1310, PubMed (Abstract only).

Wanten et al., "*Immune Modulation by Parenteral lipid Emulsions*," American Journal of Clinical Nutrition 2007;85:1171-84, American Society for Nutrition.

Driscoll et al., "*Pharmacopeial Compliance of Fish Oil-Containing Parenteral Lipid Emulsion Mixtures: Globule Size Distribution (GSD) and Fatty Acid Analyses*," International Journal of Pharmaceutics, 379 (2009), pp. 125-130, Elsevier B.V.

Wang et al., "*ω-3 Fatty Acids—Supplemented Parenteral Nutrition Decreases Hyperinflammatory Response and Attenuates Systemic Disease Sequelae in Severe Acute Pancreatitis: A Randomized and Controlled Study*," Journal of Parenteral and Enteral Nutrition, May/Jun. 2008, vol. 32, No. 3, pp. 236-241, Sage, The American Society for Parenteral & Enteral Nutrition.

Simoens et al., "*Inclusion of 10% Fish Oil in Mixed Medium-Chain Triacylglycerol-Long-Chain Triacylglycerol Emulsions Increases Plasma Triacylglycerol Clearance and Induces Rapid Eicosapentaenoic Acid (20:5n-3) Incorporation Into Blood Cell*

(56) References Cited

OTHER PUBLICATIONS

Phospholipids," American Journal of Clinical Nutrition 2008;88:282-88, American Society for Nutrition.

"Globule Size Distribution in Lipid Injectable Emulsions," United States Pharmacopoeia 32, Chapter <729>, 2009, Physical Tests, pp. 283-285.

"Fish Oil, Rich in Omega-3 Acids, Piscis Oleum Omega-3 Acidis Abundans," European Pharmacopoeia 6.0, Jan. 2008:1912, 2008, Monograph 1912, pp. 1893-1895.

"Omega-3-Acid Triglycerides: Omega-3 Acidorum Triglycerida," European Pharmacopoeia 5.4, Jan. 2005:1352 corrected, 2005, Monograph 1352, pp. 3995-3997.

"Triglycerides, Medium-Chain, Triglycerida Saturata Media," European Pharmacopoeia 6.0, Jan. 2008:0868, 2007, Monograph 0868, pp. 3122-3124.

Friesecke et al., "Fish oil supplementation in the parenteral nutrition of critically ill medical patients: a randomised controlled trial," Intensive Care Med, Aug. 2008;34(8):1411-20, Epub Mar. 21, 2008, PubMed (Abstract only).

Calder, "Rationale and use of n-3 fatty acids in artificial nutrition", Proc Nutr Soc, Nov. 2010;69(4):565-73, Epub May 5, 2010, Erratum in Proc Nutr Soc, May 2011;70(2):282, PubMed (Abstract only).

Notification of Transmittal of the International Search Report and the Written Opinion of the International Searching Authority, or the Declaration (Form PCT/ISA/220), International Search Report (Form PCT/ISA/210), and Written Opinion of the International Searching Authority (Form PCT/ISA/237), dated Jan. 6, 2011, issued in corresponding International Application No. PCT/US2010/000723 (11 pages).

Extended Search Report issued by the European Patent Office issued in corresponding European Patent Application No. 10751124.8 dated Feb. 1, 2012 (5 pages).

Carpentier, Yvon et al., "Rapid Cellular Enrichment of Eicosapentaenoate After a Single Intravenous Injection of a Novel Medium-Chain Triacylglycerol:Fish-Oil Emulsion in Humans," American Journal of Clinical Nutrition, Feb. 10, 2010, pp. 1-8, doi: 10.3945/ajcn.2009.27951, American Society for Nutrition, Bethesda, Maryland, USA.

Abulrob, A.N., et al., "The effect of fatty acids and analogues upon intracellular levels of doxorubicin in cells displaying P-glycoprotein mediated multidrug resistance", J Drug Target, pp. 247-256, (2000) 8(4) (abstract only).

Calviello, G., et al., "Docosahexaenoic acid enhances the susceptibility of human colorectal cancer cells to 5-fluorouracil", Cancer Chemother Pharmacol, Jan. 2005, pp. 12-20, 55(1) (abstract only).

Elzinga, L., et al., "Modification of experimental nephrotoxicity with fish oil as the vehicle for cyclosporine", Transplantation, Feb. 1987, pp. 271-274, 43(2) (abstract only).

Fracasso, P.M., et al., "Phase 1 and pharmacokinetic study of weekly docosahexaenoic acid-paclitaxel, Taxoprexin, in resistant solid tumor malignancies", Cancer Chemother Pharmacol, Feb. 2009, pp. 451-458, 63(3) (abstract only).

Futamura, Y., "Toxicity of amiodarone on mouse pulmonary endothelial cells cultured with or without alveolar macrophages", J Toxicol Sci, Nov. 1996, pp. 253-267, 21(4) (abstract only).

Germain, E., et al., "Anthracycline-induced cardiac toxicity is not increased by dietary omega-3 fatty acids", Pharmacol Res, Feb. 2003, pp. 111-117, 47(2) (abstract only).

Heller, A.R., et al., "Omega-3 fatty acids improve the diagnosis-related clinical outcome", Crit Care Med, Apr. 2006, pp. 972-979, 34(4) (abstract only).

Julien, C., et al., "Postmortem brain fatty acid profile of levodopa-treated Parkinson disease patients and parkinsonian monkeys", Neurochem Int,, Apr. 2006, pp. 404-414, 48(5) (abstract only).

Mahéo, K., et al., "Differential sensitization of cancer cells to doxorubicin by DHA: a role for lipoperoxidation", Free Radic Biol Med, Sep. 2005, pp. 742-751, 39(6) (abstract only).

Menendez, J.A., et al., "Exogenous supplementation with omega-3 polyunsaturated fatty acid docosahexaenoic acid (DHA; 22:6n-3) synergistically enhances taxane cytotoxicity and downregulates Her-2/neu (c-erbB-2) oncogene expression in human breast cancer cells", Eur J Cancer Prev, Jun. 2005, pp. 263-270, 14(3) (abstract only).

Priyamvada, S., et al., "Studies on the protective effect of dietary fish oil on gentamicin-induced nephrotoxicity and oxidative damage in rat kidney", Prostaglandins Leukot Essent Fatty Acids, Jun. 2008, pp. 369-381, 78(6) (abstract only).

Rudra, P.K., et al., "Cell-specific enhancement of doxorubicin toxicity in human tumour cells by docosahexaenoic acid", Anticancer Res, Jan.-Feb. 2001, pp. 29-38, 21(1A) (abstract only).

Wang, Y., et al., "Synthesis and preliminary antitumor activity evaluation of a DHA and doxorubicin conjugate", Bioorg Med Chem Lett, Jun. 1, 2006, pp. 2974-2977, 16(11) (abstract only).

Wichmann, M.W., et al., "Evaluation of clinical safety and beneficial effects of a fish oil containing lipid emulsion (Lipoplus, MLF541): data from a prospective, randomized, multicenter trial", Crit Care Med, Mar. 2007, pp. 700-706, 35(3) (abstract only).

Yang, W., et al., "Attenuation of ciclosporin-induced nephrotoxicity by dietary supplementation of seal oil in Sprague-Dawley rats", J Pharm Pharmacol, Nov. 2005, pp. 1485-1492, 57(11) (abstract only).

Colas, Séverine, et al., "Sensitization by dietary docosahexaenoic acid of rat mammary carcinoma to anthracycline: a role for tumor vascularization", Clin Cancer Res, Oct. 1, 2006, pp. 5879-5886, 12(19), American Association for Cancer Research, USA.

Ding, Wei-Qun, et al., "Differential sensitivity of cancer cells to docosahexaenoic acid-induced cytotoxicity: the potential importance of down-regulation of superoxide dismutase 1 expression", Mol Cancer Ther, Sep. 2004, pp. 1109-1117, 3(9), American Association for Cancer Research, USA.

González-Périz, Ana, et al., "Docosahexaenoic acid (DHA) blunts liver injury by conversion to protective lipid mediators: protectin D1 and 17S-hydroxy-DHA", FASEB J, Dec. 2006, FJ Express Summary pp. 2537-2539, FJ Express Full Length Article pp. E1844-E1855, 20(14), FASEB, USA.

Harries, M., et al., "Phase I/II study of DHA-paclitaxel in combination with carboplatin in patients with advanced malignant solid tumours", Br J Cancer, Nov. 1, 2004, pp. 1651-1655, 91(9), Cancer Research, UK.

Manni, Andrea, et al., "The impact of fish oil on the chemopreventive efficacy of tamoxifen against development of N-methyl-N-nitrosourea-induced rat mammary carcinogenesis", Cancer Prev Res.(Phila Pa), Mar. 2010, pp. 322-330, 3(3), American Association for Cancer Research, USA.

Matta, José A., et al., "TRPV1 is a novel target for omega-3 polyunsaturated fatty acids", J Physiol, Jan. 15, 2007, pp. 397-411, 578(Pt 2), The Physiological Society, UK.

Bougnoux, P., et al., "Improving outcome of chemotherapy of metastatic breast cancer by docosahexaenoic acid: a phase II trial," British Journal of Cancer, 2009, pp. 1978-1985, vol. 101, No. 12, , Cancer Research UK.

Driscoll, David F., "Lipid Injectable Emulsions: Pharmacopeial and Safety Issues," Pharmaceutical Research, Sep. 2006, pp. 1959-1969, vol. 23, No. 9, Springer Science + Business Media, Inc., NY, USA.

Driscoll, David F., Letter to the Editor, Journal of Parenteral and Enteral Nutrition, Jul./Aug. 2009, pp. 451-452, vol. 33, No. 4, The American Society for Parenteral & Enteral Nutrition, http://pen.sagepub.com.

Lowell, J.A., et al., "Postoperative fluid overload: not a benign problem," Crit Care Med, Jul. 1990;18(7):728-733, PubMed (Abstract only).

Mathru, Mali, et al., "Effect of Fast vs Slow Intralipid Infusion on Gas Exchange, Pulmonary Hemodynamics, and Prostaglandin Metabolism," Clinical Investigations in Critical Care, Chest, Feb. 1991, pp. 426-429, 99, American College of Chest Physicians, USA.

Prasertsom, W., et al., "Pulmonary vascular resistance during lipid infusion in neonates," Arch Dis Child, 1996;74:F95-98, Children's Health Centre and Perinatal Research Centre, University of Alberta, CA.

(56) References Cited

OTHER PUBLICATIONS

Ling, P.R., et al., "Inflammatory mediators in patients receiving long-term home parenteral nutrition," *Digestive Disease Science*, Nov. 2001;46(11):2484-9, PubMed (Abstract only).

Driscoll, David F., et al., "The influence of medium-chain triglycerides on the stability of all-in-one formulations," *International Journal of Pharmaceutics*, 2002, pp. 1-10, 240, Elsevier Science B.V., The Netherlands.

Bistrian, Bruce R., "Clinical Aspects of Essential Fatty Acid Metabolism; Jonathan Rhoads Lecture," *Journal of Parenteral and Enteral Nutrition*, 2003, pp. 168-175, vol. 27, No. 3, Sage, The American Society for Parenteral & Enteral Nutrition, http://pen.sagepub.com/content/27/3/168.

Gura, K.M., et al., "Use of a fish oil-based lipid emulsion to treat essential fatty acid deficiency in a soy allergic patient receiving parenteral nutrition," *Clinical Nutrition*, Oct. 2005;24(5):839-47, PubMed (Abstract only).

Wales, P.W., et al., "Neonatal short bowel syndrome: a cohort study," *Journal of Pediatric Surgery*, May 2005;40(5):755-62, PubMed (Abstract only).

Paquot, N., et al., "Fatty liver in the intensive carenit," *Curr Opin Clin Nutr Metab Care*, Mar. 2005;8(2):183-87, PubMed (Abstract only).

Lee, J.S., et al., "Saturated, but not n-6 polyunsaturated, fatty acids induce insulin resistance: role of intramuscular accumulation of lipid metabolites," *J Appl Physiol*, May 2006;100(5):1467-74, PubMed (Abstract only).

Gura, Kathleen M., et al., "Reversal of Parenteral Nutrition-Associated Liver Disease in Two Infants With Short Bowel Syndrome Using Parenteral Fish Oil: Implications for Future Management," *Pediatrics*, Jul. 2006, pp. e197-e201, vol. 118, No. 1, American Academy of Pediatrics, USA.

Stanley, J.C., et al., "UK Food Standards Agency Workshop Report: the effects of the dietary n-6: n-3 fatty acid ratio on cardiovascular health," *British Journal of Nutrition*, Dec. 2007; 98(6):1305-1310, PubMed (Abstract only).

Wanten, Geert JA, et al., "Immune modulation by parenteral lipid emulsions," *American Journal of Clinical Nutrition* 2007, pp. 1171-1184, 85, American Society for Nutrition, USA.

Driscoll, David F., et al., "Pharmacopeial compliance of fish oil-containing parenteral lipid emulsion mixtures: Globule size distribution (GSD) and fatty acid analyses," *International Journal of Pharmaceutics*, 2009, pp. 125-130, vol. 379, Elsevier B.V., The Netherlands.

Wang, Xinying, et al., "ω-3 Fatty Acids—Supplemented Parenteral Nutrition Decreases Hyperinflammatory Response and Attenuates Systemic Disease Sequelae in Severe Acute Pancreatitis: A Randomized and Controlled Study," *Journal of Parenteral and Enteral Nutrition*, May/Jun. 2008, pp. 236-241, vol. 32, No. 3, Sage, The American Society for Parenteral & Enteral Nutrition, http://pen.sagepub.com/content/32/3/236.

Simoens, Christina M., et al., "Inclusion of 10% fish oil in mixed medium-chain triacylglycerol-long-chain triacylglycerol emulsions increases plasma triacylglycerol clearance and induces rapid eicosapentaenoic acid (20:5n-3) incorporation into blood cell phospholipids," *American Journal of Clinical Nutrition*, 2008, pp. 282-88, vol. 88, American Society for Nutrition, USA.

"Globule Size Distribution in Lipid Injectable Emulsions," United States Pharmacopeia 32, Chapter <729>, 2009, pp. 283-285, Physical Tests.

"Fish Oil, Rich in Omega-3 Acids, Piscis Oleum Omega-3 Acidis Abundans," *European Pharmacopoeia 6.0*, Jan. 2008:1912, 2008, pp. 1893-1895, Monograph 1912.

"Omega-3-Acid Triglycerides: Omega-3 Acidorum Triglycerida," *European Pharmacopoeia 5.4*, Jan. 2005:1352 corrected, 2005, pp. 3995-3997, Monograph 1352.

"Triglycerides, Medium-Chain, Triglycerida Saturata Media," *European Pharmacopoeia 6.0*, Jan. 2008:0868, 2007, pp. 3122-3124, Monograph 0868.

Friesecke, S., et al., "Fish oil supplementation in the parenteral nutrition of critically ill medical patients: a randomised controlled trial," *Intensive Care Med*, Aug. 2008;34(8):1411-20, Epub Mar. 21, 2008, PubMed (Abstract only).

Calder, P.C., "Rationale and use of n-3 fatty acids in artificial nutrition", *Proc Nutr Soc*, Nov. 2010;69(4):565-73, Epub May 5, 2010, Erratum in Proc Nutr Soc, May 2011;70(2):282, PubMed (Abstract only).

"PrestoBlue™ Cell Viability Reagent", Life Technologies, http://www.invitrogen.com/site/us/en/home/brands/Molecular-Probes/Key-Molecular-Probes-Products/PrestoBlue-Cell-Viability-Reagent.html, 2012, Life Technologies Corporation.

Mansour, N.R., et al., "Comparison of microscopy and alamar blue reduction in a larval based assay for schistosome drug screening," *PloS Negl Trop Dis*, Aug. 2010, 4(8):e795, PubMed (Abstract only).

Nociari, M.M., et al., "A novel one-step, highly sensitive fluorometric assay to evaluate cell-mediated cytotoxicity," *J Immunol Methods*, Apr. 1998, 213(2):157-67, PubMed (Abstract only).

Hamid, R., et al., "Comparison of alamar blue and MTT assays for high through-put screening," *Toxicol In Vitro*, Oct. 2004, 18(5):703-10, PubMed (Abstract only).

Van Der Harst, M.R., et al., "Gentamicin Nephrotoxicity—A Comparison of In Vitro Findings with In Vivo Experiments in Equines," *Veterinary Research Communications*, 2005, 29(3), pp. 247-261, Springer.

Al-Nasiry, S., et al., "The use of Alamar Blue assay for quantitative analysis of viability, migration and invasion of choriocarcinoma cells," *Human Reproduction*, May 2007, 22(5):1304-09, Epub Feb. 16, 2007, PubMed (Abstract only).

Sykes, M.L., et al., "Development of an Alamar Blue™ Viability Assay in 384-Well Format for High Throughput Whole Cell Screening of *Trypanosoma brucei brucei* Bloodstream Form Strain 427," *Am J Trop Med Hyg*, 2009, 81(4), pp. 665-674, The American Society of Tropical Medicine and Hygiene, USA.

Calder, P.C., et al., "The 2008 ESPEN David Cuthbertson Lecture: Fatty acids and inflammation—from the membrane to the nucleus and from the laboratory bench to the clinic," *Clin Nutr*, Feb. 2010, 29(1):5-12, PubMed (Abstract only).

European Pharmacopoeia 5.0, "Omega-3-Acid Triglycerides", Monographs N-O, pp. 2144-2146.

European Office Action (Opposition Brief) issued Jul. 23, 2014, by the European Patent Office in corresponding European Patent Application No. EP 2 320 949, and an English Translation of the Office Action. (35 pages).

EPAX 4510 TG, product specification from the year 2004, prior art according to Article 54(2) EPC (retrieval of the archive page on Apr. 25, 2014) and EPAX 4510 TG, product specification as of Oct. 26, 2011.

Porsgaard et al., "Gastric emptying in Rats following Administration of a Range of Different Fats Measured as Acetaminophen Concentration in Plasma", Annals of nutrition and metabolism, 2003, 47(3-4), 132-138.

Driscoll, "Lipid Injectable Emulsions", Nutrition in Clinical Practice, 2006, 21(4), 381-386.

Driscoll et al., "The influence of medium-chain triglycerides on the stability of all-in-one formulations", International Journal of Pharmaceutics, 2002, 240(1), 1-10.

Ali et al., "Effect of Fish Oil Treatment on Gentamicin Nephrotoxicity in Rats", Annals of nutrition and metabolism, 1994, 38(6), 336-339.

Abdel-Gayoum et al., "Effects of fish oil and sunflower oil supplementations on gentamicin-induced nephrotoxicity in rat", Human & experimental toxicology, 1995, 14(11), 884-888.

Priyamvada et al., "Studies on the protective effect of dietary fish oil on gentamicin-included nephrotoxicity and oxidative damage in rat kidney", Science Direct, Prostaglanding, Leukotrienes and Essential Fatty Acids, 2008, 78(6), 369-381.

Notice of Allowance issued in U.S. Appl. No. 12/382,196 dated Apr. 16, 2012.

Office Action issued in U.S. Appl. No. 12/923,257 dated Nov. 15, 2012.

(56) References Cited

OTHER PUBLICATIONS

Office Action issued in U.S. Appl. No. 13/230,316 dated Jul. 11, 2013.
Office Action issued in U.S. Appl. No. 13/230,316 dated Aug. 30, 2013.
Notice of Allowance issued in U.S. Appl. No. 13/230,316 dated Aug. 4, 2014.
Office Action issued in U.S. Appl. No. 13/230,316 dated Oct. 24, 2013.
Omegaven package insert, Oct. 1, 2002.
Notice of Allowance issued in U.S. Appl. No. 13/230,316 dated Nov. 24, 2014.
Qi et al., "Triglycerides in Fish Oil Affect the Blood Clearance of Lipid Emulsions Containing Long- and Medium-Chain Triglycerides in Mice", Journal of Nutrition, 2006, vol. 136, pp. 2766-2772.
Schlotzer et al., "Elimination and tolerance of a New Parenteral Lipid Emulsion (SMOF)—A Double-Blind cross-Over study in Healthy Male Volunteers", Annals of Nutrition and Metabolism, 2004, vol. 48, pp. 263-268.
Peltier et al., "Preferential enrichment of liver phospholipids in docosahexaenoate relative to eicosapentaenoate in ω-3-depleted rats injected with a medium-chain triglyceride: Fish oil emulsion", Prostaglandins, Leukotrienes and Essential Fatty Acids, 2008, vol. 78, pp. 27-32.
International Search Report issued in International Application No. PCT/US2011/001567 on May 12, 2011.
Interlocutory decision in Opposition proceedings dated Feb. 18, 2016, by the European Patent Office in corresponding European Application No. 10 751 124.8 (U.S. Pat. No. 2,320,949).
Wikipedia, Route of administration, https://en.wikipedia.org/wiki/Route_of_administration [Jul. 7, 2015].
Adina T. Michael-Titus, "Omega-3 fatty acids and neurological injury," Science Direct, 2007, pp. 295-300, Elsevier.
Aiguo Wu et al. "Dietary Omega-3 Fatty Acids Normalize BDNF Levels, Reduce Oxidative Damage, and Counteract Learning Disability after Traumatic Brain Injury in Rats," Journal of Neurotrauma, 2004, pp. 1457-1467, vol. 21, No. 10, Mary Ann Liebert, Inc.
Omegaven—Report Nr. 5/2001, Fresenius Kabi Deutschland GmbH (2001) (discussed in Interlocutory decision in Opposition proceedings).
Yoshihiro Futamura, "Effect of Amiodarone on Release of Cytokines from Mouse Alveolar Macrophages Pretreated with Eicosapentaenoic Acid," Jpn. J. Pharmacol, 69, 1995, pp. 335-341.
John R. Senior, "Medium Chain Triglycerides," 1968, p. 277, Division of Graduate Medicine University of Pennsylvania.
Board of Appeal of the European Patent Office, dated Nov. 28, 2001, T 0432/98-3.3.2 (discussed in Interlocutory decision in Opposition proceedings).
Driscoll, U.S. Appl. No. 12/923,257, entitled "Method of Mitigating Adverse Drug Events Using Omega-3 Fatty Acids as a Parenteral Therapeutic Drug Vehicle", filed in the U.S. Patent and Trademark Office on Sep. 10, 2010.

\* cited by examiner

OMEGA-3 ENRICHED FISH OIL-IN-WATER PARENTERAL NUTRITION EMULSIONS

CROSS-REFERENCE TO RELATED APPLICATION

This application is a continuation of U.S. application Ser. No. 13/255,828 filed Nov. 1, 2011, which is a 35 USC §371 national stage application of International Application No. PCT/US2010/000723 filed on Mar. 11, 2010, which is a continuation-in-part of U.S. application Ser. No. 12/382,196 filed on Mar. 11, 2009, wherein the entire contents of each of the above applications are incorporated herein by reference.

BACKGROUND

Field

The present disclosure relates to an emulsion and a composition containing at least omega-3 acid triglycerides and a medium-chain triglyceride. The emulsion can be an oil-in-water emulsion. The emulsion and composition can be used, for example, in parenteral administration.

Related Art

Oil-in-water parenteral emulsions have been used clinically for nutritional and medical purposes. Of the various types of oils used, historically soybean oil was first introduced almost 50 years ago and thus has the greatest clinical experience.

Parenteral emulsions are described in International Publication No. WO 97/19683, U.S. Pat. No. 5,874,470 and U.S. Patent Application Publication No. 2004/0247693.

U.S. Patent Application Publication No. 2004/0247693 discloses an isotonic lipid emulsion including (i) about 60 to about 95% by weight of medium chain triglycerides, and (ii) about 5 to 40% by weight of fish oil, based on the total amount of lipids in the emulsion, under the proviso that the emulsion does not contain vegetable oils.

SUMMARY

According to an exemplary aspect, an emulsion is provided comprising:
an oil component and a water component, the oil component comprising:
  fish oil triglycerides in an amount of about 60% to about 90% based on the weight of the oil component;
    wherein the fish oil triglycerides comprise omega-3 fatty acids, expressed as triglycerides, in an amount of at least 60%, based on the total weight of the fatty acids of the fish oil triglycerides;
    wherein the fish oil triglycerides comprise a total amount of EPA and DHA, expressed as triglycerides, of at least 45%, based on the total weight of the fatty acids of the fish oil triglycerides; and,
  at least one medium-chain triglyceride oil, wherein a total amount of the at least one medium-chain triglyceride oil is from about 10% to about 40% based on the weight of the oil component.

According to another exemplary aspect, an oil composition suitable for use as an oil component of an oil-in-water emulsion is provided, comprising:
  fish oil triglycerides in an amount of about 60% to about 90% based on the weight of the composition;
    wherein the fish oil triglycerides comprise omega-3 fatty acids, expressed as triglycerides, in an amount of at least 60% based on the total weight of the fatty acids of the fish oil triglycerides;
    wherein the fish oil triglycerides comprise a total amount of EPA and DHA, expressed as triglycerides, of at least 45%, based on the total weight of the fatty acids of the fish oil triglycerides; and,
  at least one medium-chain triglyceride oil, wherein a total amount of the at least one medium-chain triglyceride oil is from about 10% to about 40% based on the weight of the composition.

According to another exemplary aspect, an emulsion is provided comprising:
an oil component and a water component, the oil component comprising:
  fish oil triglycerides in an amount of greater than 50% to about 90% based on the weight of the oil component of the emulsion;
    wherein the fish oil triglycerides comprise omega-3 fatty acids, expressed as triglycerides, in an amount of at least 60%, based on the total weight of the fatty acids of the fish oil triglycerides;
    wherein the fish oil triglycerides comprise a total amount of EPA and DHA. expressed as triglycerides, of at least 45%, based on the total weight of the fatty acids of the fish oil triglycerides; and, a medium-chain triglyceride oil.

According to another exemplary aspect, an emulsion is provided comprising:
an oil component and a water component, the oil component comprising:
  fish oil triglycerides in an amount of about 31% to about 90% based on the weight of the oil component of the emulsion;
    wherein the fish oil triglycerides comprise omega-3 fatty acids, expressed as triglycerides, in an amount of at least 60%, based on the total weight of the fatty acids of the fish oil triglycerides;
    wherein the fish oil triglycerides comprise a total amount of EPA and DHA, expressed as triglycerides, of at least 45%, based on the total weight of the fatty acids of the fish oil triglycerides; and,
  a medium-chain triglyceride;
  wherein the emulsion is an oil-in-water emulsion, and wherein the concentration of the oil component in the emulsion is 5 g/100 mL to less than 20 g/100 mL, or the concentration of the oil component in the emulsion is greater than 20 g/100 mL to 30 g/100 mL.

According to another exemplary aspect, an emulsion is provided comprising:
an oil component and a water component, the oil component comprising:
  fish oil triglycerides present in an amount of about 31% to about 90% based on the weight of the oil component of the emulsion;
    wherein the fish oil triglycerides comprise omega-3 fatty acids, expressed as triglycerides, in an amount of at least 60%, based on the total weight of the fatty acids of the fish oil triglycerides;
    wherein the fish oil triglycerides comprise a total amount of EPA and DHA, expressed as triglycerides, of at least 45%, based on the total weight of the fatty acids of the fish oil triglycerides;
  a medium-chain triglyceride oil; and
  a vegetable oil.

According to another exemplary aspect, an emulsion is provided comprising:
an oil component and a water component, the oil component comprising:

fish oil triglycerides present in an amount of about 31% to about 90% based on the weight of the oil component of the emulsion;
   wherein the fish oil triglycerides comprise omega-3 fatty acids, expressed as triglycerides, in an amount of at least 60%, based on the total weight of the fatty acids of the fish oil triglycerides;
   wherein the fish oil triglycerides comprise a total amount of EPA and DHA, expressed as triglycerides, of at least 45%, based on the total weight of the fatty acids of the fish oil triglycerides; and, a medium-chain triglyceride;
wherein the emulsion is an oil-in-water emulsion, and wherein the concentration of the oil component in the emulsion is 5 g/100 mL to 17.5 g/100 mL, or the concentration of the oil component in the emulsion is 22.5 g/100 mL to 30 g/100 mL.

According to another exemplary aspect, an oil-in-water emulsion is provided comprising:
   a) fish oil triglycerides consisting of glycerol which is esterified with fatty acids wherein said fatty acids comprise EPA and DHA in an amount of at least 45% by weight of said fatty acids and the total amount of omega-3 fatty acids is at least 60% by weight of said fatty acids, and
   b) at least one medium chain triglyceride oil, and
wherein the fish oil triglycerides are present in an amount of at least 51% by weight based on the total weight of the oil component, and the medium chain triglycerides are present in an amount of 10 to 49% by weight based on the total weight of the oil component.

According to another exemplary aspect, the fish oil triglycerides are present in an amount ranging from 51 to 90% by weight based on the total weight of the oil component.

According to another exemplary aspect, the oil component additionally comprises a vegetable oil.

According to another exemplary aspect, the vegetable oil is present in an amount of up to 10 percent by weight, preferably from 2 to 8% by weight based on the total weight of the oil component of the oil-in-water emulsion.

According to another exemplary aspect, the vegetable oil is selected from the group consisting of soybean oil and safflower oil and mixtures thereof.

According to another exemplary aspect, the oil-in-water emulsion comprises the oil component in an amount ranging from 5 to 30 g/100 mL, preferably 15 to 25 g/100 mL, for example, 20 g/100 mL of the emulsion.

According to another exemplary aspect, the oil-in-water emulsion additionally comprises at least one phospholipid emulsifier component which is preferably selected from the group of phospholipids derived from egg or soya.

According to another exemplary aspect, the phospholipid emulsifier component is a phosphatidyl choline.

According to another exemplary aspect, the phospholipid emulsifier component is present in a weight ratio of phospholipid to triglycerides ranging from 0.05 to 0.07, preferably 0.06.

According to another exemplary aspect, the oil-in-water emulsion additionally comprises an isotonic agent, preferably in a concentration ranging from 20 to 25 g/L.

According to another exemplary aspect, the oil-in-water emulsion comprises glycerol as isotonic agent.

According to another exemplary aspect, the oil-in-water emulsion comprises a pH-adjusting agent.

According to another exemplary aspect, the oil-in-water emulsion comprises sodium oleate as the pH adjusting agent.

According to another exemplary aspect, the pH adjusting agent is present in a concentration of up to 3 g/L.

According to another exemplary aspect, the pH value of the emulsion ranges from 6 to 9, preferably from 6 to 8.5, more preferably from 7.5 to 8.5.

According to another exemplary aspect, the oil-in-water emulsion additionally comprises an antioxidant which is preferably present in a concentration of up to 1 g/L.

According to another exemplary aspect, the antioxidant is α-tocopherol.

According to another exemplary aspect, the emulsion is parenterally applicable.

According to another exemplary aspect, the mean droplet diameter of the oil droplets is below 250 nm, preferably below 240 nm at 20° C.

According to another exemplary aspect, a pharmaceutical composition is provided comprising or consisting of an oil-in-water emulsion.

According to another exemplary aspect, a pharmaceutical composition is provided for use in the prophylaxis or treatment of the group of diseases consisting of systemic inflammatory response syndrome (SIRS), respiratory distress syndrome (RDS), nutritional and/or dietary cause of liver disease, an iatrogenic cause of liver disease, a pathological cause of liver disease, an immune modulation, head trauma, post operative surgical stress, a myocardial infarction and cystic fibrosis.

According to another exemplary aspect, a composition is provided that includes an enriched fish oil according to Pharm Eur 1352 specifications which is a "processed oil" that is fortified to contain a higher proportion of the bioactive omega-3 fatty acids compared to natural sources.

According to another exemplary aspect, a composition is provided that includes an omega-3 essential fatty acid (EFA), and an omega-6 EFA of a fish oil, wherein the omega-6 EFA is present in an amount that minimizes a negative clinical impact from excessive intakes of the pro-inflammatory fatty acid mediators.

According to another exemplary aspect, an emulsion is provided in which a final o/w emulsion concentration is from about 5 g/100 mL to about 30 g/100 mL, for example, a concentration of about 20 g/100 mL.

According to another exemplary aspect, a composition is provided that includes medium-chain fatty acids (FAs) of a medium-chain triglyceride (MCT) oil, wherein the medium-chain FAs are present in amounts effective to facilitate the metabolic clearance of fish oil. For example, the MCTs can be present in an amount that is effective to facilitate the metabolic clearance of long-chain triglycerides.

According to another exemplary aspect, the MCTs can function as a suitable energy source that is at least equal or comparable in its nitrogen-sparing properties to long chain triglycerides, but without metabolic consequence to inflammatory processes in patients.

According to another exemplary aspect, a composition is provided that includes MCTs in amounts effective to maintain the stability of the emulsion.

According to another exemplary aspect, there is a reduction of the concentration of saturated long-chain fatty acids (LCFAs) in the oil source of the emulsion which can result in a reduction of adverse clinical effects such as inflammation, glucose intolerance and/or insulin resistance.

According to another exemplary aspect, the composition of the oil phase of the emulsion can be adjusted to optimize the response to intravenous nutritional support.

According to another exemplary aspect, a composition of the oil phase of the emulsion is provided that can include n3-FAs in an amount that is effective to exert a desirable pharmacological effect, for example, to combat deleterious inflammatory responses or preserve vital organ functions.

According to another exemplary aspect, a composition is provided that can include an optimal balance of triglycerides in order to reduce or eliminate the toxicity that can result from the parenteral administration of conventional o/w emulsions.

DETAILED DESCRIPTION

An exemplary embodiment is directed to a novel parenteral lipid emulsion composition comprising: a relatively high concentration of an oil derived from fish oil triglycerides, that is highly enriched in long-chain omega-3 (n-3) fatty acids (n3-FAs); a relatively low concentration of medium-chain fatty acids from medium chain triglycerides (MCTs); and optionally an amount of long-chain omega-6 (n-6) fatty acids (n6-FAs).

As used herein, the terms "fish oil" and "fish oils" pertain to constituents such as triglycerides which are present in a fish oil, and constituents such as triglycerides which are derivatives or products obtained from a fish oil. In an exemplary embodiment, fish oil triglycerides described herein include triglycerides derived or synthesized from a fish oil. For example, the fish oil triglycerides can include a synthetically derived oil containing re-esterified omega-3 fatty acids, which have been derived from a fish oil. For example, the synthetically derived oil can be derived from a fish oil in accordance with an enrichment process that is effective to separate desirable fatty acids (such as omega-3 fatty acids, for example, EPA and DHA) from, for example, certain undesirable fatty acids (for example, saturated long-chain FAs). An example of such enrichment process is separation by molecular distillation and/or filtration. In an exemplary embodiment, the synthetically derived oil can be derived in a manner that is consistent with EP 1352, discussed below.

The oil that is derived from fish oil can contain n3-FAs at a concentration higher than that occurring in natural sources. The medium-chain fatty acids from medium chain triglycerides (MCTs) can be saturated medium-chain fatty acids. The n6-FAs can be provided from a vegetable oil, for example, in order to meet EFA requirements. In one embodiment, the composition of such as an emulsion can be stable, has normal metabolic clearance, and/or is well-tolerated by patients. For example, the emulsion can be an oil-in-water (o/w) emulsion.

An exemplary oil is derived from fish, and can be rich in the polyunsaturated and bioactive omega-3 fatty acids. The oil component of the emulsion can contain fish oil triglycerides, for example, rich in omega-3 acid triglycerides. The fish oil triglycerides, can be present from about 31% to about 90%, or from about 41% to about 90%, or from about 45% to about 90%, or from greater than 50% to about 90%, or from about 51% to about 90%, or from about 55% to about 90%, or from about 60% to about 90%, or from about 61% to about 90%, or from about 70% to about 90%, or from about 71% to about 90%, or from about 80% to about 90%, or from about 40% to about 80%, or from about 50% to about 70%, or from about 60% to about 65%, based on the total weight of the oil component of the emulsion. For example, by employing exemplary ranges of fish oil triglycerides, the amount of esterified omega-3 fatty acids delivered to a human body can be increased. For example, Applicant has recognized the clinical significance of the absolute intake of omega-3 fatty acids, and that such absolute intake of omega-3 fatty acids can be increased by employing, for example, the exemplary ranges of fish oil triglycerides. For example, Applicants have recognized that in at least some applications, for example cardiovascular health indications, the absolute intake of omega-3 fatty acids can be a more accurate indicator of overall efficacy than the ratio of omega-3 fatty acids to omega-6 fatty acids. See, for example, Stanley et al, 2007.

The fish oil triglycerides can be 20- to 22-carbon compounds and can contain 3 or more double bonds located at the $3^{rd}$ position from the methyl end of the long-chain fatty acid (LCFA) molecule. Standard notation for the various fatty acids (FAs) includes: 1) carbon number, followed by, 2) the number of double bonds, and ending with 3) the position of the double bond relative to the methyl position (or "n3" in the case of the LCFA from fish oil). In particular, the marine oil can be highly enriched with two major n3-FAs, i.e., eicosapentaenoic acid, or EPA (20:5n3), and docosahexaenoic acid, or DHA (22:5n3). The marine oil can contain lesser amounts of other n3-FAs, such as docosapentaenoic acid, or DPA (22:6n3). The fish oil component of the o/w parenteral lipid emulsion can represent oils from a mixture of fatty fish families, such as from the following species: Engraulidae (e.g., anchovies), Carangidae (e.g., mackerel), Clupeidae (e.g., herring), Osmeridae (e.g., smelt), Salmonidae (e.g., salmon) and Scombridge (tuna).

In the European Pharmacopeia (EP), there are two monographs (i.e., EP 1352 entitled "Omega-3 Acid Triglycerides", and, EP 1912 entitled "Fish Oil, Rich in Omega-3 Acids") that pertain to fish oil (EP 1352, EP 1912, 2008). The monograph EP 1352 substantially differs from EP 1912 in that the composition and requirements for the bioactive n3-FAs in EP 1352 are much higher than in EP 1912 (EP 1352: EPA+DHA≥45%; total n3-FAs≥60% vs. EP 1912: EPA: ≥13%; DHA≥9%; total n3-FAs≥28%). The levels of n3-FAs in EP 1912 are consistent with those found in nature. By comparison, in EP 1352, the n3-FA concentrations are substantially higher and can be obtained by an enrichment process such as molecular distillation, whereby certain undesirable LCFAs that are present, for example, myristic acid, palmitic acid and stearic acid, are removed. In so doing, the concentrations of all FAs present, and particularly the n3-FAs, are proportionately elevated (Driscoll, 2008a).

In an exemplary embodiment, the fish oil triglycerides can include omega-3 fatty acids, expressed as triglycerides, in an amount of at least 60%, based on the total weight of the fatty acids of the fish oil triglycerides. In an exemplary embodiment, the fish oil triglycerides can include a total amount of EPA and DHA, expressed as triglycerides, of at least 45%, based on the total weight of the fatty acids of the fish oil triglycerides. For example, a fatty acid that is expressed as a triglyceride can be referred to as an esterified fatty acid. For example, the fatty acids and omega-3 fatty acids (such as, for example, EPA and DHA) discussed herein refer to the constituent parts of such acids in a fish oil triglyceride, in accordance with EP 1352. For example, the fatty acids and omega-3 fatty acids (such as, for example, EPA and DHA) discussed above can be in their esterified form when present in the fish oil triglycerides.

The fish oil triglycerides can contain at least one n6-FA, for example, a plurality of n6-FAs. The at least one n6-FA can include, for example, arachidonic acid or AA, (20:4n6) and linoleic acid or LA, (18:2n6). Additionally or alternatively, the n3-FA, alpha linolenic acid or ALA, (18:3n3) can be present. For example, the total content of the at least one n6-FA can be from about 0.1% to about 1.0%, or from about 0.2% to about 0.9%, or from about 0.3% to about 0.8%, or from about 0.4% to about 0.7%, or from about 0.5% to about 0.6%, based on the weight of the oil component of the emulsion.

An exemplary second component of the oil component of the emulsion can include at least one medium chain triglyceride (MCT) oil, for example, at a plurality of exemplary MCT concentrations. For example, the at least one MCT oil can be present from about 10% to about 69%, or from about 10% to about 40%, or from about 10% to about 30%, or from about 10% to about 20%, or from about 10% to about 15%, or from about 20% to about 60%, or from about 30% to about 50%, or from about 40% to about 45%, based on the total weight of the oil component of the emulsion. For example, by employing exemplary ranges of MCT concentrations, the amount of esterified omega-3 fatty acids delivered to a human body can be increased. For example, by employing exemplary MCT concentrations, the amount of esterified omega-3 fatty acids delivered to a human body can be increased with usage of a relatively smaller amount of MCTs, while still achieving beneficial metabolic clearance and physicochemical stability characteristics of the emulsion.

For example, the at least one MCT oil can include saturated medium chain fatty acids, for example, a plurality of saturated medium chain fatty acids. In an exemplary embodiment, the MCTs include a mixture of fatty acids having from 6 to 12 carbon atoms. The MCT oil can be derived from a plant such as a fruit or vegetable, for example, a plurality of plants. The MCT oil can contain caprylic acid (for example, in an amount of about 50% to about 80% by weight of the MCT oil), an 8-carbon saturated FA (8:0). The MCT oil can contain capric acid (for example, in an amount of about 20% to about 50% by weight of the MCT oil), a 10-carbon saturated FA (10:0). For example, the medium-chain triglycerides can contain caprylic acid and capric acid, in an amount of at least 90% by weight of the MCT oil. The description of the MCT oil for use in this disclosure can, for example, meet the requirements of EP monograph 0868, entitled "Triglycerides, Medium Chain" (*Triglycerida saturate* media) (EP 0868, 2008).

The oil component can optionally include a vegetable oil. The vegetable oil can include, for example, soybean oil, safflower oil or a combination thereof. The vegetable oil can, for example, be rich in the n6-FA, LA, and/or can contain lesser amounts of the n3-FA, ALA.

The emulsion can optionally include at least one additional ingredient, a pharmaceutical adjuvant. The at least one additional ingredient can include, for example, egg phospholipid, sodium oleate, glycerol, alpha-tocopherol and sodium hydroxide and/or sterile water. Such ingredients can be used, for example, to stabilize the emulsion and make suitable its use for intravenous administration in accordance with pharmacopeial specifications.

Oil-in-water parenteral emulsions can be used clinically for nutritional and medical purposes. Of the various types of oils used, historically soybean oil was first successfully introduced in the clinical setting almost 50 years ago and thus has generated the greatest clinical experience, but more recent formulations have included other oils, such as MCT, fish and olive oils. As a nutritional supplement, o/w parenteral emulsions are intended for use in patients having a dysfunctional gastrointestinal tract, originating from, for example, mesentery artery thrombosis, requiring a massive small bowel resection that produces a condition known as "short bowel syndrome". Consequently, such patients have insufficient intestine and therefore are incapable of absorbing sufficient macronutrients (protein, carbohydrate and fat) and micronutrients (electrolytes, vitamins and minerals). There are other clinical indications for intravenous nutrition (e.g., radiation enteritis, bowel obstruction, high output ileostomies, etc.) that may also require life-long intravenous nutrition. In other clinical cases, intravenous nutrition is used as a temporary therapeutic maneuver, for example, in critically ill patients to support the body's metabolic response to injury and infection. In the absence of oral intake, these catabolic conditions can produce large daily losses of vital body protein and profound energy deficits. If prolonged or accompanied by pre-existing malnutrition, the absence of nutritional intervention may increase the risk of significant clinical morbidity or mortality (Driscoll, 2008b).

In the case of o/w parenteral emulsions containing fish oil, these emulsions can provide the essential fatty acids (EFAs) from both the n-3 FA, EPA, DHA and the n-6 FA, AA, which cannot be synthesized by the body. In the case of parenteral o/w emulsions containing soybean oil, these emulsions can provide the precursors to these EFAs in the form of ALA for n3-FAs and LA for n6-FAs. Again, historically, the introduction of soybean oil was based on providing sufficient concentrations of ALA (7 to 11%) and very high amounts of LA (50 to 55%) to prevent EFA deficiency. To meet the EFA requirements with soybean oil-based parenteral emulsions, between 1 and 4% of daily minimum calories are required (Bistrian, 2003). Thus, for example, in a 2000 kcal adult diet, 1% of caloric intake (as LA or ~50% of soybean oil) would translate to approximately 40 kcals, or a minimum of about 3.5 g of soybean oil per day (equal to 17.5 mLs of a 20% lipid emulsion); for a 100 kcal neonate diet, 1% of caloric intake would translate to 2 kcal (about 0.2 g per day, or 1 mL of the soybean oil emulsion) in order to meet EFA requirements.

In addition to being a source of EFAs, parenteral lipid emulsions can also be prescribed as a daily source of energy or calories, often in substitution of a portion of the calories that would be provided as carbohydrate (hydrated dextrose or glucose), administered intravenously. The practice of prescribing both glucose and lipids as energy sources (or a "mixed-fuel system") can be done to avoid significant metabolic complications associated with high doses of intravenous glucose. These include hyperglycemia and increased infectious risks, hepatic damage from the metabolic conversion of glucose to fat in the liver, increased respiratory dysfunction from excessive carbon dioxide production associated with hepatic lipogenesis in patients with impaired lung function, and other adverse effects. As a daily source of calories, fat intake from parenteral lipid emulsions is commonly prescribed in amounts ranging between 20 and 40% of total caloric intake. Thus, for example, in a 2000 kcal adult diet, this represents 400 to 800 kcals, or approximately 44 to 88 g per day, which is equal to about 220 to 440 mLs per day of a 20% oil-in-water emulsion. For a neonatal diet of 100 kcals per day, this would equate to 20 to 40 kcals, or approximately 2.2 to 4.4 g per day, equal to about 10 to 20 mLs per day of the same 20% lipid emulsion.

Although a soybean oil-based parenteral emulsion was the first safe intravenous o/w dispersion introduced in 1961, and therefore the formulation most widely used worldwide, soybean oil is not the optimal lipid to use in the clinical setting. As a long-chain triglyceride (LCT) of plant origin, the most abundant "omega" fatty acid found in this oil is the polyunsaturated, essential (precursor) n6-FA, LA (50-55%), followed by the monounsaturated, non-essential n9-FA, oleic acid (18:1 n9) (24-26%), followed by the polyunsaturated essential (precursor) n3-FA, ALA (7 to 11%). Due to the dominant presence of the n6-FA, LA, and considering both its pro-inflammatory role and the fact that it is a precursor to the highly vasoactive "2-series" eicosanoids involving prostagladins and thromboxanes, as well as the potent immunomodulatory "4-series" leukotrienes, soybean oil may adversely accentuate the systemic inflammatory response and/or exacerbate the deterioration of certain functions of vital organs. During critical illness accompanied by systemic inflammatory response syndrome (SIRS), for example, the "2-series" eicosanoids produced from the infusion of soybean oil-based parenteral emulsions may worsen lung function in patients with respiratory distress syndrome. In adults, for example, infusions of soybean oil-based lipid emulsions have produced two different adverse effects on the lungs, which have been shown to be infusion rate-dependent (Mathru et al, 1991). In one case, infusions of 100 g of a 20% soybean oil-based parenteral emulsion (i.e., 500 mL) over 10 hours was associated with significantly increased shunt fraction from pre-infusion levels presumably via prostaglandin-mediated pulmonary vasodilatation. This action is counter to the normal physiologic response when blood flow proportionately decreases to poorly ventilated segments of the lung during respiratory distress, known as hypoxic pulmonary vasoconstriction. This results in an unphysiologic mismatch between the normally balanced ventilation and perfusion in the lungs, where the body now makes futile attempts to perfuse poorly ventilated areas of the lung. In contrast, the same infusion, but now infused over only 5 hours, has been shown to produce the opposite effect, i.e., vasoconstriction, evidenced by significant increases in mean pulmonary artery pressure, which can also aggravate respiratory function by augmenting the hypoxic pulmonary vasoconstrictive response to potentially pathological proportions (e.g., pulmonary hypertension). Similar adverse pulmonary responses have been associated with the infusion of parenteral lipid emulsions rich in n6-FAs in infants (Prasertsom et al, 1996).

Another clinical example demonstrating the potential deleterious effects associated with the administration of conventional soybean oil-based parenteral emulsions, rich in the pro-inflammatory n6-FAs, involves hepatotoxicity. For example, in acutely ill infants with SIRS, prolonged infusion of soybean oil-based parenteral emulsions may induce a pathological condition known as parenteral nutrition-associated liver disease or PNALD. The PNALD condition often occurs with long-term use of parenteral nutrition in infants and may lead to liver failure and the need for liver transplantation. Clinical findings associated with PNALD include abnormal elevations of blood components observed in liver function tests, such as serum transaminases, bilirubin and alkaline phosphatase, due to hepatic fat accumulation, leading ultimately to organ failure (Gura et al, 2006). The mechanism of liver injury is not completely understood but has been suggested to occur by a "two-hit" theory. The first "hit" occurs during the accumulation of fat in the liver, or hepatic steatosis. The second "hit" that follows occurs in a series of subsequent steps beginning with inflammation and cellular degeneration, followed by production of reactive oxygen species or peroxidation products causing oxidative stress, that ultimately causes damage of liver tissue (Paquot et al, 2005). In infants developing PNALD, mortality approaches 100% within one year of the diagnosis (Wales et al., 2005). Adverse effects to the liver from chronic exposure to soybean oil parenteral emulsions have been linked to adults requiring long-term parenteral nutrition (Ling et al, 2001).

Clearly, therefore, in an exemplary embodiment, parenteral lipid emulsions containing high amounts of triglycerides rich in n6-FAs are not optimal, and are associated with significant adverse events in patients requiring intravenous nutrition. Therefore, development of alternative lipid sources that decrease the concentration of n-6 FAs and their accompanying pro-inflammatory effects may be of great clinical benefit. The use of n9-FAs found in olive oil, such as the monounsaturated fatty acids that are less pro-inflammatory, may be of significant benefit. The use of n3-FAs, however, such as the polyunsaturated fatty acids producing the "3-series" eicosanoids, may be of the greatest clinical benefit. In fact, the latter n3-FAs from the important omega families of fatty acids that have shown great promise and are the least pro-inflammatory, have also been shown to possess favorable effects on vital organs, and produce important immunomodulatory effects (Wanten, 2007). Thus, the ideal parenteral lipid emulsion would be one that is stable, provides a sufficient supply of the EFAs, provides a dense source of energy or calories, minimizes the adverse effects from pro-inflammatory FAs, improves functions of vital organs, and possesses therapeutically beneficial immunomodulatory effects, particularly during acute illness.

Exemplary embodiments disclosed herein employ a new composition of matter containing oils, for example, from MCTs and LCTs, with novel doses of the various saturated medium-chain fatty acids (for example, 8- to 10-carbon MCFAs) and, mainly unsaturated long-chain fatty acids (for example, 18- to 22-carbon LCFAs) from the biologically important, essential FAs from n3 and n6 families. In the final oil composition of the parenteral o/w lipid emulsion, the resulting oil phase can be made as a simple "physical" mixture or blend of the desired oils. Alternatively, specifically customized mixtures of "structured" triglycerides can be made via hydrolysis of FAs from the glycerol backbones of different oils, followed by random transesterification producing both preferred as well as analog triglyceride combinations. Or, the "structured" triglycerides can be made via enzymatic synthesis by selected lipases that are region-specific, e.g., sn-1 and sn-3 positions, and FA-specific, producing a purer form of chemically defined structured triglycerides. No matter how they are prepared, the resulting emulsions are composed of mixtures of various triglycerides and fatty acids, primarily from fish oil and MCT oil, and are mixed in specific proportions. In either case, when provided within the ranges and specifications of Table 1, the formulations can yield novel final lipid mixtures that serve as: 1) a dense source of calories, containing: 2) a highly enriched fish oil as the major lipid source; 3) minimum, but sufficient, amounts of the omega-6 fatty acids; 4) sufficient amounts of MCT oil to facilitate its metabolic clearance upon intravenous infusion; 5) sufficient amounts of MCT oil to facilitate the stability of the emulsion; and/or 6) optionally, a small fraction of soybean oil as an additional source of essential fatty acids for omega-6 requirements.

In an exemplary embodiment, the concentration of oil in the emulsion can be any suitable concentration. For example, the final concentration of oil in the formulation can be 20% oil-in-water or 20 g per 100 mL of emulsion. More generally, for example, the amount of the oil component in the oil-in-water emulsion can be from 5 g/100 mL to 30 g/100 mL. In an exemplary embodiment, the amount of the oil component in the oil-in-water emulsion can be 5 g/100 mL to 17.5 g/100 mL, or the amount of the oil component in the emulsion can be 22.5 g/100 mL to 30 g/100 mL.

The composition of the final formulation can be customized to optimize the ratios of all ingredients to address a wide array of clinical and pharmaceutical issues. In addition, a given formulation may also desirably contain a specific ingredient, or set of specific ingredients, for the purpose of addressing one or more particular medical conditions and/or pharmaceutical purposes, thus yielding several variations in composition to produce several different formulations. For example, in the treatment of critically ill patients with systemic inflammatory response syndrome, providing relatively high amounts of omega-3 acid triglycerides can, for example, counter the deleterious effects of excessive inflammation. As well, pharmaceutical benefits can be derived from fish oil containing high concentrations of the bioactive n3-FAs, for example, when used as a drug carrier vehicle to counter the effects of drugs affecting vital end organs such as nephrotoxicities, so that renal blood flow can be maintained by the countervailing effects of the prostaglandins derived from the "3-series" versus deleterious ischemic effects from the "2-series". Exemplary ranges of fish oil and MCT oil concentrations are set forth in Table 1. The specific concentrations of the emulsion constituents can depend on the desired treatment.

Table 2 provides a sample of various oil combinations, expressed as weight percentages of each of the triglycerides. In an exemplary embodiment, only highly-enriched fish oil, in compliance with EP monograph 1352 (EP 1352, 2008), can be the fish oil source along with a certain amount of MCT oil, also in compliance with EP monograph 0868 (EP 0868, 2008), to comprise the total lipid fraction (for example, 20 g of oil per 100 mL of emulsion) in the current application. In an exemplary embodiment, a reduced concentration of saturated LCFAs can be employed to avoid potential complications such as insulin resistance (Lee et al, 2006), which can be one clinical issue of interest to the critically ill.

In an exemplary embodiment, the oil component of the emulsion can include a vegetable oil. The vegetable oil can include, for example, soybean oil, safflower oil and/or a combination thereof. The vegetable oil can be present in an amount of up to 10%, or from about 1% to about 10%, or from about 2% to about 9%, or from about 3% to about 8%, or from about 4% to about 7%, or from about 5% to about 6%, based on the weight of the oil component of the emulsion. For example 2 g of vegetable oil such as soybean oil can be present per 20 g of total oil per 100 mL of emulsion.

The vegetable oil, such as soybean oil, can be employed in the event that use thereof is deemed clinically advantageous or necessary to increase the dose of the omega-6 FAs in a given formulation. For example, the use of a vegetable oil such as soybean oil can be advantageous to provide additional nutritional support. For example, the vegetable oil such as soybean oil can be used in the treatment of a patient requiring lifelong intravenous nutrition support where, for example, meeting the n6-FA requirements of these patients solely via fish oil in fish oil-MCT mixtures may not be sufficient to avoid a deficiency state especially when all nutritional ingredients can only be provided via the intravenous route of administration.

In exemplary embodiments, the amount of vegetable oil (such as, for example, soybean oil and/or safflower oil) can be restricted to comprise no more than about 10% by weight of the total oil component, whereas in current formulations, concentrations of vegetable oil vary typically from 20 to 100% by weight of the oil component of the emulsion. For example, the vegetable oil can be present from 0% to about 10%, or from about 1% to about 9%, or from about 2% to about 8%, or from about 3% to about 7%, or from about 4% to about 6% based on the total weight of the oil component of the emulsion. There are numerous combinations and permutations that can be derived from the present compositions. Therefore, it should be understood that those specific combinations represented in Table 2 are merely intended to illustrate representative combinations and are not meant to be inclusive or restrictive in any way. Hence, the possibility of additional variations would be clear to those skilled in the art.

For example, the fish oil emulsion intended in this application can be one that contains a high concentration or the highest concentration possible of the bioactively important n3-FAs, which are best able to deliver a wide range of potential clinical benefits by altering lipids in the blood and the structure and function of cell membranes. For example, Increasing the absolute intakes of n3-FAs in order to improve cardiovascular health can be a clinical benefit, for example, rather than basing treatment on the n6:n3 ratio as originally thought (Stanley J C et al., 2007), and can be effective to achieve similar clinical benefits in other inflammatory conditions. Providing higher amounts of n3-FAs in relation to n6-FA intakes can result in displacement of AA in cell membranes by EPA, and a shift away from the highly vasoactive and pro-inflammatory eicosanoids of the "2-series" in favor of the less vasoactive "3-series". These actions can lead to a favorable modulation of the metabolic and immune response to injury and infection, particularly in various scenarios in the acute care setting (e.g., multiple organ failure, head trauma, sepsis, burns and inflammatory bowel disease). Thus, the source (and subsequent dose) of fish oil intended in this application can have substantial and clinically beneficial effects. The fish oil triglycerides can include omega-3 fatty acids, expressed as triglycerides, in an amount of at least 60%, based on the total weight of the fatty acids of the fish oil triglycerides. The fish oil triglycerides can include a total amount of EPA and DHA, expressed as triglycerides, of at least 45%, based on the total weight of the fatty acids of the fish oil triglycerides. In an exemplary embodiment, the fish oil triglycerides can include a total amount of EPA and DHA, expressed as triglycerides, of at least 45%, based on the total weight of the fatty acids of the fish oil triglycerides. For example, the minimum concentration specified can be equal to the sum of EPA and DHA, expressed as triglycerides, ≥45% of the n3-FA profile, and the total n3-FA content (e.g., EPA+DHA+DPA)≥60% by weight from the selected fish oil source. This specification is in conformance with the requirements of EP monograph 1352 (EP 1352, 2008). Of the three current, commercially available products containing fish oil, two comply with the lower limits (i.e., EPA≥13%; DHA≥9%; Total n3-FA≥28%) associated with EP monograph 1912 (EP 1912, 2008). The concentration of fish oil in the only currently available formulation that meets EP 1352 is only 10% by weight of the oil component of the emulsion, whereas in this application, for example, the minimum percentage by weight of the oil component of the emulsion containing the specified highly enriched fish oil source can be 31%. The amount of bioactive n3-FAs in fish oil described in this disclosure can be more than double the amounts more commonly found for clinical use as specified by weight of oil source in the two different EP monographs (e.g., EP 1352, total n3-FA: ≥260%; vs. EP 1912, total n3-FA: ≥28%).

One aspect of an exemplary formulation is to deliver a high concentration of enriched fish oil triglycerides having, for example, the highest concentration available that meets a high standard or the highest pharmacopeial standards, for example, in order to maximize the clinical benefits of the n3-FAs in a variety of clinical conditions, such as the systemic inflammatory response syndrome, or SIRS, characteristically found in critically ill patients. In fact, the blood concentrations of C-reactive protein, a biomarker of SIRS, was found to be significantly reduced in critically ill patients with pancreatitis receiving n3-FAs, as compared to those patients receiving lipids as n6-FAs (Wang, 2008). As inflammation accompanies all forms of acute metabolic stress, the delivery of highly concentrated n3-FAs may reduce inflammation and improve outcome in the treatment of many medical conditions. Moreover, since fluid overload is also a major problem in the intensive care unit, use of highly concentrated n3-FAs would reduce the volume burden, an important clinical issue in the care of critically ill patients (Lowell et al, 1990). In addition, the total dose of lipids delivered would be only one-half the amount according to this disclosure for current emulsions that conform to EP 1912, compared to using a fish oil source as detailed in this application that meets the higher specifications of EP 1352, thus, for example, reducing or avoiding excessive lipid intakes (both quantity and quality of fatty acids delivered) that may affect its metabolic clearance.

Exemplary formulations described in this disclosure can be designed to contain a sufficient amount of the essential FAs associated with (or obtained from): 1) the n3 family, i.e., EPA (20:5n3), DHA (22:6n3) and small amounts of its precursor, linolenic acid (18:3n3); and, 2) the omega-6, or n6, family, arachidonic acid (20:4n6), or AA, as well as small amounts of its precursor, linoleic acid (18:2n6). With regard to meeting the essential n3-FA requirements, this goal can be easily met by both the recommended concentrations of fish oil in the formula, as well as from a highly enriched source of n3-FAs, as per the specifications of EP 1352. The amount of the essential n6-FAs employed can be specifically designed to be minimized in exemplary formulations, but in modest amounts that are still large enough to prevent EFA deficiency. For example, meeting the n-6 FA requirements can be achieved through the use of a fish oil-MCT mixture, owing to the fact that the average amount of AA found in fish oil is approximately 0.5%. Therefore, because the amount of FA needed as AA is approximately one-tenth the dose required if provided through its precursor, LA, EFA requirements are thus met. For example, to prevent EFA deficiency by providing LA by parenteral administration, at least 1% of the total daily caloric intake should be provided (Bistrian, 2003). As stated previously, in a 2000 kcal per day diet, the minimum intake of LA would be 2.2 g per day, or approximately 3.5 g of soybean oil (~55% LA); in terms of AA, the requirements for the same diet would be approximately 0.2 g per day; in a 1500 kcal per day diet, 1.6 g of LA, or ~0.16 g of AA, per day would be needed; in a 1000 kcal per day diet, 1.1 g of LA, or ~0.11 g of AA, would be needed; in a 500 kcal per day diet, 0.55 g of LA, or ~0.05 g of AA would be needed; and finally, in a 100 kcal per day diet, 0.11 g of LA would be needed, or 0.01 g as AA per 100 calories. As can be seen in Table 3, which provides sample compositions for Fish Oil-MCT mixtures only, the EFA requirements for n6-FAs, coming from AA in the fish oil, would be met in the 80% fish oil-20% MCT oil mixture as presented. This does not include the additional source of n6-FAs that comes from the LA normally present in fish oil. It should also be recognized that certain compositions or formulations of products derived from this description, for example, can be intended for short-term parenteral administration during critical illness, for example, rather than for patients susceptible to EFA deficiency. In other cases, where EFA supplementation is a clinical concern, alternative formulations can be devised that contain very low amounts of soybean oil (for example, up to 10%) of the total oil phase. Table 4 provides exemplary formulations using a fixed 60:40 ratio (by weight) of fish oil to MCT oil, with increasing fractions of soybean oil, ranging from 1 to 5%. The "fixed" fish oil-MCT ratio shown in Table 4 is merely illustrative and not meant to be exclusive or restrictive in any way as to the various oil ratios that are possible based on this disclosure.

An exemplary final concentration of oil in exemplary formulations is a 20% oil-in-water emulsion (20 g oil mixture per 100 mL of emulsion). This overall oil concentration can be consistent with the oil concentration in administered lipid emulsions used clinically, and it can be associated with better plasma clearance compared to "10%" formulations, as the optimum phospholipid-triglyceride (PL:TG) ratio for parenteral lipid emulsions appears to be about 0.06 (1.2 g PL:20 g TG) (Driscoll et al., 2001). Nonetheless, there are multiple variations in the final concentration of oil in mixtures that can be devised in exemplary embodiments, as long as the PL:TG ratio of 0.06 is maintained. A sample of the possible formulations is shown in Table 5.

The concentrations of MCT oil in various possible formulations can be sufficient to facilitate the clearance of the long-chain triglycerides in fish oil (20-carbon EPA and 22-carbon DHA), which has been shown to occur in other mixtures (Simoens et al., 2008). Exemplary ratios (by weight) of MCT to omega-3 LCT in this application can be different from that found in other parenteral lipid emulsion mixtures containing both of these oils. For this reason, exemplary amounts described in this application are unique and the resulting formulations can benefit from assessment to confirm the favorable effect on plasma clearance of LCTs in the presence of MCTs. Additionally or alternatively, the clearance of these formulations can be facilitated by optimizing the infusion rate, for example, in accordance with its normal metabolic clearance.

The concentrations of MCT oil in the various possible formulations can be sufficient to facilitate the physicochemical stability of the long-chain triglycerides in fish oil (20-carbon EPA and 22-carbon DHA), which has been shown to occur in other mixtures. (Driscoll et al., 2002). Exemplary ratios (by weight) of MCT to omega-3 LCT described in this application can be different from other parenteral lipid emulsion mixtures containing both of these oils. For this reason, the relative and absolute amounts of each type of oil that are used in this application can be unique and the resulting formulations can benefit from assessment to confirm the favorable effect on emulsion stability of LCTs in the presence of MCTs.

In an exemplary embodiment, the amounts of saturated LCFAs in an emulsion can be modified, for example, so as to lower the concentration thereof from what is present in natural sources. For example, a specific reduction in the concentrations of LCFAs, such as palmitic acid (16:0), can help to reduce the risk of insulin resistance (Lee et al, 2006), which can be particularly relevant in acutely ill patients. In addition, for example, by effectively increasing the proportion of highly enriched polyunsaturated n3-FAs, such as EPA (20:5n3) and DHA (22:6n3), in accordance with EP 1352, and by increasing the proportion of the highly enriched fish oil triglycerides in the oil component of the emulsion as described, this can reduce the concentrations of the saturated LCFAs that can produce potentially deleterious adverse effects.

Exemplary parenteral lipid emulsions can optionally contain vegetable oil as an additional source of n6-FAs, in addition to the amounts already present in the fish oil. For example, the soybean oil can be present as a very small fraction (by weight of the oil component of the emulsion).

The soybean oil can be employed, for example, in a case where EFA deficiency is considered to pose a significant clinical risk, such as in patients receiving life-long parenteral nutrition support. In this patient population, nutrient deficiencies can develop, for example, if there is little to no gastrointestinal absorption of nutrients via oral intake. In this circumstance, a higher intake of n6-FAs via parenteral lipid emulsion may be desirable. Table 4 provides an exemplary sample of possible formulations, where the soybean oil content is increased progressively up to a level of 5% by weight of the oil component of the emulsion. In addition, the use of higher n3-FA proportions (up to 90%) in various possible formulations can, for example, also increase n6-FA intake.

Exemplary formulations produced as described herein can be designed to provide a unique, but dense, source of calories that are, for example, equally nitrogen-sparing as in conventional or current parenteral lipid emulsions. The final parenteral lipid formulation can ideally be an isotonic energy source that can be provided in small volumes when possible. This can be particularly advantageous, for example, in the case of acutely ill patients who may be volume-overloaded as a result of receiving multiple intravenous fluids for medical purposes, such as for resuscitation and maintenance of blood pressure, kidney function and intravenous medications.

According to an exemplary aspect, a composition comprising an enriched fish oil triglycerides as a lipid source is provided.

In another exemplary aspect, the composition comprises at least 45% by weight of EPA and DHA, expressed as triglycerides, and at least 60% by weight of n3-FA, expressed as triglycerides, based on the total weight of the composition.

In another exemplary aspect, the composition is an oil-in-water emulsion having an oil derived from an enriched fish oil of from about 31% to about 90% by weight of the oil component of the emulsion.

In another exemplary aspect, a method of administering the composition (such as, for example, an emulsion) is provided comprising administering the composition to a human body, wherein the oil component of the emulsion contains a sufficient concentration of n3-FAs to provide an effective dose.

In other exemplary aspects, the administered dose of n3-FAs is capable of the safe treatment of systemic inflammatory response syndrome (SIRS); the dose is capable of the safe treatment of respiratory distress syndrome (RDS); the dose is capable of the safe treatment of nutritional/dietary causes of liver disease; the dose is capable of the safe treatment of iatrogenic causes of liver or kidney disease; the dose is capable of the safe treatment of pathological causes of liver or kidney disease; the dose is capable of the safe treatment of immune modulation; the dose is capable of the safe treatment of head trauma; the dose is capable of the safe treatment of postoperative surgical stress; the dose is capable of the safe treatment of myocardial infarction; and/or the dose is capable of the safe treatment of cystic fibrosis.

In another exemplary aspect, a composition is provided comprising omega-3 essential fatty acids and omega-6 essential fatty acids of a fish oil, wherein the essential fatty acids are present in amounts effective to minimize an impact of excessive amounts of pro-inflammatory fatty acids.

In another exemplary aspect, a method of administering the composition is provided comprising administering the composition to a human body.

In another exemplary aspect, an amount of the omega-6 essential fatty acid is capable of the safe treatment to mitigate or prevent EFA deficiency when the range of fish oil is from 31% and 90%, by weight of the oil component of the emulsion, in the absence of soybean oil.

In another exemplary aspect, an amount of the omega-6 essential fatty acid is capable of the safe treatment for mitigation or prevention of EFA deficiency when the range of concentration of fish oil triglycerides is from about 31% to about 90% by weight of the oil phase of the emulsion in the absence of soybean oil. To further mitigate or prevent EFA deficiency when the range of fish oil is between 31% and 90%, the concentration of additional soybean oil can be between 1 and 10%, by weight of the oil component of the emulsion.

In another exemplary aspect, an amount of the omega-6 essential fatty acid is capable of the safe treatment of medical conditions without exerting clinically significant adverse effects related to eicosanoid metabolism.

In another exemplary aspect, an amount of the omega-6 essential fatty acid does not interfere with or counteract the dose of n3-FAs present.

In another exemplary aspect, a composition is provided comprising medium-chain fatty acids of an MCT oil, wherein the medium-chain fatty acids are present in an amount effective to facilitate a metabolic clearance of fish oil.

In another exemplary aspect, the MCT oil is present in an amount of from about 10% to about 69%, by weight of the oil component of the emulsion, and the amount of the MCT oil allows for the safe plasma clearance of the fish oil.

In other exemplary aspects, the dose of lipids infused is incorporated into cell membranes; the dose of lipids infused generates eicosanoids of the 3-series; and/or the dose of lipids infused does not produce clinically significant hypertriglyceridemia.

In another exemplary aspect, a composition is provided comprising medium-chain triglycerides of an oil, wherein the medium-chain triglycerides are present in an amount effective to facilitate stability.

In another exemplary aspect, a composition is provided wherein the MCT oil concentration is from about 10% to about 69%, by weight of the oil component of the emulsion, and the fish oil concentration is from about 31% to about 90%, by weight of the oil component of the emulsion, and wherein the concentrations allow for physicochemical stability of the composition for from about 18 to about 24 months.

In another exemplary aspect, the MCT oil concentration is from about 10% to about 69%, the fish oil concentration is from about 31% to about 90%, by weight of the oil component of the emulsion, and a soybean oil concentration is up to about 10%, by weight of the oil component of the emulsion, and wherein the concentrations allow for physicochemical stability of the composition in its original container for from about 18 to about 24 months.

In another exemplary aspect, the MCT oil concentration is from about 10% to about 69%, by weight of the oil component of the emulsion, and the fish oil concentration is from about 31% to about 90%, by weight of the oil component of the emulsion, and wherein the concentrations allow for physicochemical stability of the composition as used in an extemporaneously prepared syringe for up to 12 hours at temperatures up to 40° C.

In another exemplary aspect, the MCT oil concentration is from about 10% to about 69%, by weight of the oil component of the emulsion, and the fish oil concentration is from about 31 to about 90%, by weight of the oil component of the emulsion, and a soybean oil concentration is up to about 10%, for example up to about 5%, by weight of the oil component of the emulsion, wherein the concentrations allow for the physicochemical stability of the composition as used in an extemporaneously prepared syringe for up to 12 hours at temperatures up to 40° C.

In another exemplary aspect, the MCT oil concentration is from about 10% to about 69%, by weight of the oil component of the emulsion, and the fish oil concentration is from about 31% to about 90%, by weight of the oil component of the emulsion, and the concentrations allow for the physicochemical stability of the composition as an extemporaneously TPN admixture for up to 24 hours at temperatures up to 40° C.

In another exemplary aspect, the MCT oil concentration is from about 10% to about 69%, by weight of the oil component of the emulsion, the fish oil concentration is from about 31% to about 90%, by weight of the oil component of the emulsion, and a soybean oil concentration is up to 10%, by weight of the oil component of the emulsion, and the concentrations allow for the physicochemical stability of the composition as used in an extemporaneously prepared TPN admixture for up to 24 hours at temperatures up to 40° C.

In another exemplary aspect, the composition provides a source of calories that is equally nitrogen-sparing as a soybean parenteral oil-in-water emulsion.

In another exemplary aspect, the composition provides a sufficient amount of egg phospholipids in proportion to the triglyceride oil phase, in order to stabilize the emulsion.

In another exemplary aspect, the composition provides a sufficient amount of egg phospholipids in proportion to the triglyceride oil phase, in order to not interfere with the clearance or breakdown of the infused lipid droplets.

In another exemplary aspect, the composition provides a sufficient amount of α-tocopherol as an anti-oxidant to protect the highly polyunsaturated n-3 fatty acids present.

In another exemplary aspect, a composition is provided comprising fatty acids of a fish oil and medium-chain triglycerides, wherein the composition is an oil-in-water emulsion comprising an oil phase and an aqueous phase.

In another exemplary aspect, the enriched fish oil is present in an amount from about 31% to about 90%, by weight of the oil component of the emulsion.

In another exemplary aspect, the medium-chain triglycerides are is present in an amount from about 10% to about 69%, by weight of the oil component of the emulsion.

In another exemplary aspect, a method of parenteral administration of the composition is provided comprising parenterally administering the composition to a human body.

The examples described herein are not meant to be inclusive, but instead have been utilized in order to form exemplary embodiments of the disclosure. It should be understood that manipulation of specific concentrations of total ingredients, including, for example, specific compositions and proportions of each ingredient within the specified concentration ranges, may be advantageous in order to achieve a specific optimal outcome. In the present disclosure, exemplary aspects can yield unique parenteral lipid emulsions appropriate for special medical purposes.

As already described herein, exemplary emulsions can have various final compositions and characteristics depending on the specific application of the emulsion. In an exemplary embodiment, the emulsion can be in compliance with the specifications set forth in United States Pharmacopoeia (USP) Chapter <729> entitled "Globule Size Distribution in Lipid Injectable Emulsions" (United States Pharmacopoeia, 2009), the contents of which are incorporated herein by reference. The two exemplary globule size limits include: 1) the intensity-weighted mean droplet size that is less 500 nanometers obtained by dynamic or static light scattering methods; and, 2) the volume-weighted percent of fat greater than five micrometers or PFAT5 that is less than 0.05% obtained by light extinction employing single-particle optical sensing methods.

The emulsion can have any suitable physical and chemical characteristics such as droplet size, and pH, free fatty acids, etc. For example, the emulsion can possess physical characteristics which facilitate its use in parenteral administration applications. In an exemplary embodiment, an emulsion can have a mean droplet size of, for example, less than 500 nm, or less than 250 nm, or less than 240 nm, or from 230 to 240 nm. In an exemplary embodiment, an emulsion can have a $PFAT_5$ value of less than 0.05%.

Exemplary physical and chemical embodiments were prepared and tested to confirm that such embodiments comply with specifications, for example, specification set forth in USP <729> and exemplary manufacturing specifications. To exemplify the pharmaceutical feasibility of the exemplary emulsions containing relatively high amounts of omega-3 acid triglycerides, for example, about 60% to about 90% by weight of the oil component, along with relatively low amounts of MCT, for example, about 10% to about 40% by weight of the oil phase, exemplary lipid emulsions 1 and 2 were manufactured and tested having omega-3 fatty acid triglycerides-to-MCTs ratios of 90:10, and 70:30, respectively, were compared to currently available emulsions 3, 4 and 5. Various physical and chemical characteristics were measured and compared, and the results are set forth in Table 6.

As can be seen from the results, like currently available emulsions, the exemplary emulsions were in compliance with the mean size and $PFAT_5$ specifications of the United States Pharmacopoeia (USP) Chapter <729> entitled "Globule Size Distribution in Lipid Injectable Emulsions" (United States Pharmacopoeia, 2009). In addition, exemplary emulsions were in compliance with exemplary manufacturing specifications (for example pH, peroxide value, acid value, free fatty acids, phosphatidyl choline and glycerol). Such data confirms Applicant's prior understanding that exemplary emulsions are capable of compliance with various specifications.

Tables mentioned herein are set forth below:

TABLE 1

Compositions of LipOmega-3 MCT 20%

| *PHARMACEUTICAL INGREDIENT | CONCENTRATION (g/L) **(80% F.O.:20% MCT) | ***RANGE OF CONCENTRATIONS (g/L) |
|---|---|---|
| Fish Oil Major FAs | 160 | 62 to 180 |
| (36.5%) EPA (20:5n3) | 58.4 | 22.6 to 65.7 |
| (25.3%) DHA (22:6n3) | 40.5 | 15.7 to 45.5 |
| (7.0%) DPA (20:6n3) | 11.1 | 4.0 to 12.6 |
| (0.50%) AA (20:4n6) | 0.8 | 0.31 to 0.9 |
| MCT Oil | 40 | 20 to 138 |
| Soybean Oil Major FAs | 0 | 0 to 10 |
| (55%) (18:2n6) | 0 | 0.0 to 5.5 |
| (10%) (18:3n3) | 0 | 0.0 to 1.0 |
| Glycerol | 22.5 | 20 to 25 |
| Egg Phospholipids | 12 | PL:TG Ratio, 0.06 |
| Sodium Oleate | 2.5 | 0 to 3 |

TABLE 1-continued

Compositions of LipOmega-3 MCT 20%

| *PHARMACEUTICAL INGREDIENT | CONCENTRATION (g/L) **(80% F.O.:20% MCT) | ***RANGE OF CONCENTRATIONS (g/L) |
|---|---|---|
| α-tocopherol | 0.2 | 0 to 1 |
| Sterile Water for Inj. | q.s. ad 1000.0 | Fixed |

*INGREDIENT Ranges: Fish Oil: 31 to 90%; MCT Oil: 10 to 69%; Soybean Oil: 0 to 5%; Glycerol: 2.0 to 2.5%;
**Sample Formulation and g per L
***GENERAL CALCULATED RANGE: RANGES of Ingredients; not accounting for experimental errors in measurement.

TABLE 2

Sample Compositions of Possible Oil Combinations of LipOmega-3 MCT 20%

| Sample | Fish Oil (%) | MCT Oil (%) | Soybean Oil (%) |
|---|---|---|---|
| 1 | 90 | 10 | 0 |
| 2 | 80 | 20 | 0 |
| 3 | 70 | 30 | 0 |
| 4 | 60 | 40 | 0 |
| 5 | 50 | 50 | 0 |
| 6 | 40 | 60 | 0 |
| 7 | 31 | 69 | 0 |
| 8 | 90 | 9 | 1 |
| 9 | 80 | 18 | 2 |
| 10 | 70 | 27.5 | 2.5 |
| 11 | 60 | 37 | 3 |
| 12 | 50 | 46.5 | 3.5 |
| 13 | 40 | 56 | 4 |
| 14 | 31 | 64 | 5 |

TABLE 3

EFA Intakes from Sample LipOmega-3 MCT Formulations Fish Oil-MCT Oil Mixtures

| Kcals/day (20% Fat) | *Linoleic 2.2% | *Linolenic 1.5% | AA | EPA | DHA |
|---|---|---|---|---|---|
| 20 g (100 mL) of a Fish Oil 80% - MCT Oil 20% Mixture | | | | | |
| 100 (2.2 g) | 0.038 g | 0.026 g | 0.009 g | 0.64 g | 0.45 g |
| 500 (11.1 g) | 0.195 g | 0.133 g | 0.044 g | 3.24 g | 2.25 g |
| 1000 (22.2 g) | 0.391 g | 0.266 g | 0.089 g | 6.48 g | 5.62 g |
| 1500 (33.3 g) | 0.586 g | 0.399 g | 0.133 g | 9.72 g | 8.42 g |
| 2000 (44.4 g) | 0.781 g | 0.533 g | 0.178 g | 12.96 g | 11.23 g |
| 20 g (100 mL) of a Fish Oil 70% - MCT Oil 30% Mixture | | | | | |
| 100 (2.2 g) | 0.033 g | 0.023 g | 0.008 g | 0.56 g | 0.39 g |
| 500 (11.1 g) | 0.171 g | 0.117 g | 0.039 g | 2.84 g | 1.97 g |
| 1000 (22.2 g) | 0.342 g | 0.233 g | 0.078 g | 5.67 g | 3.93 g |
| 1500 (33.3 g) | 0.513 g | 0.350 g | 0.117 g | 8.51 g | 5.90 g |
| 2000 (44.4 g) | 0.684 g | 0.466 g | 0.155 g | 11.34 g | 7.86 g |
| 20 g (100 mL) of a Fish Oil 60% - MCT Oil 40% Mixture | | | | | |
| 100 (2.2 g) | 0.029 g | 0.020 g | 0.007 g | 0.48 g | 0.33 g |
| 500 (11.1 g) | 0.147 g | 0.100 g | 0.033 g | 2.43 g | 1.68 g |
| 1000 (22.2 g) | 0.293 g | 0.200 g | 0.067 g | 4.86 g | 3.37 g |
| 1500 (33.3 g) | 0.440 g | 0.300 g | 0.100 g | 7.29 g | 5.05 g |
| 2000 (44.4 g) | 0.586 g | 0.400 g | 0.133 g | 9.72 g | 6.74 g |
| 20 g (100 mL) of a Fish Oil 50% - MCT Oil 50% Mixture | | | | | |
| 100 (2.2 g) | 0.024 g | 0.017 g | 0.006 g | 0.40 g | 0.28 g |
| 500 (11.1 g) | 0.122 g | 0.083 g | 0.028 g | 2.03 g | 1.40 g |
| 1000 (22.2 g) | 0.244 g | 0.167 g | 0.056 g | 4.05 g | 2.81 g |
| 1500 (33.3 g) | 0.366 g | 0.250 g | 0.083 g | 6.08 g | 4.21 g |
| 2000 (44.4 g) | 0.488 g | 0.333 g | 0.111 g | 8.10 g | 5.62 g |
| 20 g (100 mL) of a Fish Oil 40% - MCT Oil 60% Mixture | | | | | |
| 100 (2.2 g) | 0.019 g | 0.013 g | 0.004 g | 0.32 g | 0.22 g |
| 500 (11.1 g) | 0.098 g | 0.067 g | 0.022 g | 1.62 g | 1.12 g |
| 1000 (22.2 g) | 0.195 g | 0.133 g | 0.044 g | 3.24 g | 2.25 g |
| 1500 (33.3 g) | 0.293 g | 0.200 g | 0.067 g | 4.86 g | 3.37 g |
| 2000 (44.4 g) | 0.391 g | 0.266 g | 0.089 g | 6.48 g | 4.49 g |

*Amounts of omega-6 FAs are averages from fish families in monograph 1352.

TABLE 4

EFA Intakes from Sample LipOmega-3 MCT Formulations Fish Oil-MCT Oil-Soya Oil Mixtures

| Kcals/day (20% Fat) | *Linoleic | *Linolenic | AA | EPA | DHA |
|---|---|---|---|---|---|
| 20 g (100 mL) of Fish Oil 60% - MCT Oil 39% - Soya Oil 1% | | | | | |
| 100 (2.2 g) | 0.041 g | 0.022 g | 0.007 g | 0.48 g | 0.33 g |
| 500 (11.1 g) | 0.208 g | 0.110 g | 0.033 g | 2.43 g | 1.68 g |
| 1000 (22.2 g) | 0.415 g | 0.222 g | 0.067 g | 4.86 g | 3.37 g |
| 1500 (33.3 g) | 0.623 g | 0.333 g | 0.100 g | 7.29 g | 5.05 g |
| 2000 (44.4 g) | 0.830 g | 0.444 g | 0.133 g | 9.72 g | 6.74 g |
| 20 g (100 mL) of Fish Oil 60% - MCT Oil 38% - Soya Oil 2% | | | | | |
| 100 (2.2 g) | 0.053 g | 0.024 g | 0.007 g | 0.48 g | 0.33 g |
| 500 (11.1 g) | 0.269 g | 0.122 g | 0.033 g | 2.43 g | 1.68 g |
| 1000 (22.2 g) | 0.537 g | 0.244 g | 0.067 g | 4.86 g | 3.37 g |
| 1500 (33.3 g) | 0.806 g | 0.367 g | 0.100 g | 7.29 g | 5.05 g |
| 2000 (44.4 g) | 1.074 g | 0.489 g | 0.133 g | 9.72 g | 6.74 g |
| 20 g (100 mL) of Fish Oil 60% - MCT Oil 37% - Soya Oil 3% | | | | | |
| 100 (2.2 g) | 0.065 g | 0.027 g | 0.007 g | 0.48 g | 0.33 g |
| 500 (11.1 g) | 0.330 g | 0.133 g | 0.033 g | 2.43 g | 1.68 g |
| 1000 (22.2 g) | 0.659 g | 0.266 g | 0.067 g | 4.86 g | 3.37 g |
| 1500 (33.3 g) | 0.989 g | 0.400 g | 0.100 g | 7.29 g | 5.05 g |
| 2000 (44.4 g) | 1.319 g | 0.533 g | 0.133 g | 9.72 g | 6.74 g |
| 20 g (100 mL) of Fish Oil 60% - MCT Oil 36% - Soya Oil 4% | | | | | |
| 100 (2.2 g) | 0.077 g | 0.029 g | 0.007 g | 0.48 g | 0.33 g |
| 500 (11.1 g) | 0.391 g | 0.144 g | 0.033 g | 2.43 g | 1.68 g |
| 1000 (22.2 g) | 0.781 g | 0.289 g | 0.067 g | 4.86 g | 3.37 g |
| 1500 (33.3 g) | 1.173 g | 0.433 g | 0.100 g | 7.29 g | 5.05 g |
| 2000 (44.4 g) | 1.563 g | 0.578 g | 0.133 g | 9.72 g | 6.74 g |
| 20 g (100 mL) of Fish Oil 60% - MCT Oil 35% - Soya Oil 5% | | | | | |
| 100 (2.2 g) | 0.085 g | 0.031 g | 0.007 g | 0.48 g | 0.33 g |
| 500 (11.1 g) | 0.452 g | 0.156 g | 0.033 g | 2.43 g | 1.68 g |
| 1000 (22.2 g) | 0.904 g | 0.311 g | 0.067 g | 4.86 g | 3.37 g |
| 1500 (33.3 g) | 1.356 g | 0.467 g | 0.100 g | 7.29 g | 5.05 g |
| 2000 (44.4 g) | 1.807 g | 0.622 g | 0.133 g | 9.72 g | 6.74 g |

*Includes amounts from both Fish Oil and Soya Oil.

TABLE 5

Various Sample Concentrations of the Oil Phase While
Maintaining a Phospholipid:Triglyceride ratio of 0.06

| Total Oil (g/100 mL) | Phospholipid (g/100 mL) | Fish Oil (%) | MCT Oil (%) | Soya Oil (%) |
|---|---|---|---|---|
| 5.0 | 0.30 | 90 | 10 | 0 |
| 7.5 | 0.45 | 80 | 20 | 0 |
| 10.0 | 0.60 | 80 | 15 | 5 |
| 12.5 | 0.75 | 70 | 30 | 0 |
| 15.0 | 0.90 | 70 | 29 | 1 |
| 17.5 | 1.05 | 60 | 40 | 0 |
| 20.0 | 1.20 | 60 | 36 | 4 |
| 22.5 | 1.35 | 50 | 50 | 0 |
| 25.0 | 1.50 | 50 | 47 | 3 |
| 27.5 | 1.65 | 40 | 60 | 0 |
| 30.0 | 1.80 | 31 | 69 | 0 |

TABLE 6

Physical and Chemical Profile of Exemplary and Comparative
Emulsions (20 g oil/dL) at 25° C.

| Specifications | | Emulsions | | | | |
|---|---|---|---|---|---|---|
| Parameter | Range | 1 | 2 | 3 | 4 | 5 |
| pH | 7.5-8.5 | 8.07 | 8.06 | 8.1 | 8.0 | 7.9 |
| Mean Size (nm) | 240-320 | 234 | 235 | 282 | 243 | 256 |
| PFAT$_5$ (%) | <0.05 | 0.042 | 0.034 | 0.029 | 0.018 | 0.025 |
| Peroxide Value | ≤1.0 | 0.38 | 0.40 | <0.1 | <0.1 | <0.1 |
| Acid Value | ≤0.5 | 0.14 | 0.12 | <0.2 | 0.3 | 0.3 |
| Free Fatty Acids (mmol/L) | ≤3.0 | 2.28 | 1.91 | 1.98 | 2.17 | 2.23 |
| Phosphatidyl Choline (g/L) | 7.8-10.6 | 9.53 | 9.91 | 9.13 | 8.89 | 9.13 |
| Glycerol (g/L) | 23.8-26.3 | 24.5 | 25.2 | 25.6 | 25.3 | 25.8 |

1 (exemplary) = 90% Fish Oil Triglycerides (FOT): 10% Medium Chain Triglycerides (MCTs)
2 (exemplary) = 70% FOT: 30% MCTs
3 (comparative) = Lipofundin N (100% Soybean Oil Triglycerides)
4 (comparative) = Lipofundin MCT (50% Soybean Oil Triglycerides: 50% MCTs)
5 (comparative) = Lipidem (50% MCTs: 40% Soybean Oil Triglycerides: 10% FOT)

While various embodiments are described herein, it will be appreciated that variations, modifications and other changes in form and detail may be made without departing from the spirit and scope of the disclosure. Such variations and modifications are to be considered within the purview and scope of the disclosure as defined by the appended claims.

REFERENCES

Lowell et al. Crit Care Med 1990; 18:728-733.
Mathru et al. Chest 1991; 99:426-29.
Prasertsom et al., Arch Dis Child 1996; 74:F95-98.
Ling et al. Digestive Disease Science 2001; 46:2484-9.
Driscoll et al. Lipid Emulsions in Parenteral Nutrition. In Clinical Nutrition: Parenteral Nutrition (Rombeau, Rolandelli, eds.) W.B. Saunders, 2001; pp. 35-59.
Driscoll et al. International Journal of Pharmaceutics, 2002; 240:1-10.
Bistrian, Journal of Parenteral and Enteral Nutrition, 2003; 27:168-75.
Gura et al. Clinical Nutrition 2005; 24:839-47.
Wales et al. Journal of Pediatric Surgery 2005; 40:755-62.
Paquot et al. Curr Opin Clin Nutr Metab Care 2005; 8:183-87.
Lee et al. J Appl Physiol 2006; 100:1467-74.
Gura et al. Pediatrics 2006; 118:e197-e201.
Stanley et al. British Journal of Nutrition, 2007; 98:1305-1310.
Wanten et al. American Journal of Clinical Nutrition 2007; 85:1171-84.
European Pharmacopoeia 6.0, Monograph 1352, Omega-3 Acid Triglycerides, *Omega-3 acidorum triglycerida*, 1893-95, 2008.
European Pharmacopoeia 6.0, Monograph 1912, Fish Oil, Rich in Omega-3 Acids, *Piscis oleum omega-3 acidis abundans*, 2554-56, 2008.
European Pharmacopoeia 6.0, Monograph 0868, Triglycerides, Medium-Chain, *Triglycerida saturate media*, 3122-24, 2008.
Driscoll et al, International Journal of Pharmaceutics, 2008a, In press.
Wang et al. Journa of Parenteral and Enteral Nutrition, 2008; 32:236-41.
Simoens et al. American Journal of Clinical Nutrition 2008; 88:282-88.
Driscoll et al. Parenteral and Enteral Nutrition in the Intensive Care Unit. In Intensive Care Medicine (Irwin and Rippe, eds.), Wolters Kluwer, 2008b; pp. 2187-2201.
United States Pharmacopoeia (USP) Chapter <729> entitled "Globule Size Distribution in Lipid Injectable Emulsions" (United States Pharmacopoeia, 2009).

All of the references are herein incorporated by reference in their entirety to the same extent as if each individual reference were specifically and individually indicated to be incorporated herein by reference in its entirety.

The invention claimed is:
1. An emulsion comprising:
  an oil component and a water component, wherein the amount of the oil component in the emulsion is 5 to 30 g/100 mL, the oil component comprising:
    fish oil triglycerides in an amount of about 60% to about 90% based on the weight of the oil component;
      wherein the fish oil triglycerides comprise omega-3 fatty acids, expressed as triglycerides, in an amount of at least 60%, based on the total weight of the fatty acids of the fish oil triglycerides;
      wherein the fish oil triglycerides comprise a total amount of EPA and DHA, expressed as triglycerides, of at least 45%, based on the total weight of the fatty acids of the fish oil triglycerides; and,
    at least one medium-chain triglyceride oil, wherein a total amount of the at least one medium-chain triglyceride oil is from about 10% to about 40% based on the weight of the oil component,
  wherein the emulsion comprises an egg phospholipid present in a weight ratio of egg phospholipid to triglycerides ranging from 0.05 to 0.07.
2. The emulsion of claim 1, wherein the fish oil triglycerides are present in an amount of about 70% to about 90% based on the weight of the oil component of the emulsion.
3. The emulsion of claim 1, wherein the fish oil triglycerides are present in an amount of about 80% to about 90% based on the weight of the oil component of the emulsion.
4. The emulsion of claim 1, wherein the total amount of the at least one medium-chain triglyceride oil is from about 10% to about 30% based on the weight of the oil component of the emulsion.

5. The emulsion of claim 1, wherein the total amount of the at least one medium-chain triglyceride oil is from about 10% to about 20% based on the weight of the oil component of the emulsion.

6. The emulsion of claim 1, wherein the oil component is substantially free of myristic acid, palmitic acid and stearic acid.

7. The emulsion of claim 1, wherein the amount of the oil component in the emulsion is 5 g/100 mL to 17.5 g/100 mL, or the amount of the oil component in the emulsion is 22.5 g/100 mL to 30 g/100 mL.

8. The emulsion of claim 1, comprising α-tocopherol.

9. The emulsion of claim 1, comprising an omega-6 fatty acid-containing triglyceride.

10. The emulsion of claim 1, wherein the emulsion is physicochemically stable for at least 18 months.

11. The emulsion of claim 1, wherein the emulsion is physicochemically stable as an extemporaneously prepared syringe dosage for at least 12 hours at a temperature of 40° C.

12. The emulsion of claim 1, wherein the at least one medium-chain triglyceride oil comprises caprylic acid and capric acid,
wherein the caprylic acid and capric acid constitute at least 90% by weight of the total content of the at least one medium-chain triglyceride oil.

13. The emulsion of claim 1, comprising a vegetable oil.

14. The emulsion of claim 13, wherein the vegetable oil is present in an amount of up to 10% based on the weight of the oil component of the emulsion.

15. The emulsion of claim 13, wherein the vegetable oil comprises a soybean oil, a safflower and/or a mixture thereof.

16. An emulsion comprising:
an oil component and a water component, wherein the amount of the oil component in the emulsion is 5 to 30 g/100 mL, the oil component comprising:
fish oil triglycerides in an amount of about 31% to about 90% based on the weight of the oil component;
wherein the fish oil triglycerides comprise omega-3 fatty acids, expressed as triglycerides, in an amount of at least 60%, based on the total weight of the fatty acids of the fish oil triglycerides;
wherein the fish oil triglycerides comprise a total amount of EPA and DHA, expressed as triglycerides, of at least 45%, based on the total weight of the fatty acids of the fish oil triglycerides; and,
at least one medium-chain triglyceride oil, wherein a total amount of the at least one medium-chain triglyceride oil is from about 10% to about 69% based on the weight of the oil component,
wherein the emulsion comprises an egg phospholipid present in a weight ratio of egg phospholipid to triglycerides ranging from 0.05 to 0.07.

17. The emulsion of claim 16, wherein the at least one medium-chain triglyceride oil comprises caprylic acid and capric acid,
wherein the caprylic acid and capric acid constitute at least 90% by weight of the total content of the at least one medium-chain triglyceride oil.

18. A method of administering the emulsion of claim 1, comprising parenterally administering a dose of the emulsion to a human body.

19. A method for treating a human having a condition selected from the group consisting of a systemic inflammatory response syndrome, a respiratory distress syndrome, a nutritional and/or dietary cause of liver disease, an iatrogenic cause of liver disease, a pathological cause of liver disease, an immune modulation, head trauma, postoperative surgical stress, a myocardial infarction, cystic fibrosis and a combination thereof, said method comprising parenterally administering to said human an effective dosage amount of the emulsion of claim 1.

* * * * *